(12) United States Patent
Pigott

(10) Patent No.: US 10,828,471 B2
(45) Date of Patent: Nov. 10, 2020

(54) BALLOON CATHETER HAVING A RETRACTABLE SHEATH

(71) Applicant: John P. Pigott, Sylvania, OH (US)

(72) Inventor: John P. Pigott, Sylvania, OH (US)

( * ) Notice: Subject to any disclaimer, the term of this patent is extended or adjusted under 35 U.S.C. 154(b) by 118 days.

(21) Appl. No.: 16/033,874

(22) Filed: Jul. 12, 2018

(65) Prior Publication Data

US 2018/0318564 A1 Nov. 8, 2018

Related U.S. Application Data

(63) Continuation-in-part of application No. 15/241,606, filed on Aug. 19, 2016, now Pat. No. 10,315,014, (Continued)

(51) Int. Cl.
*A61M 31/00* (2006.01)
*A61M 37/00* (2006.01)
*A61M 25/10* (2013.01)

(52) U.S. Cl.
CPC ...... *A61M 25/10184* (2013.11); *A61M 25/10* (2013.01); *A61M 25/1002* (2013.01); (Continued)

(58) Field of Classification Search
CPC .. A61M 2025/1068; A61M 2025/1081; A61M 25/10; A61M 2025/0046; A61M 2025/1079; A61M 25/0045
See application file for complete search history.

(56) References Cited

U.S. PATENT DOCUMENTS 2,655,154 A 10/1953 Richter
3,557,794 A 1/1971 Van Patten
(Continued)

FOREIGN PATENT DOCUMENTS

EP 0727194 A1 8/1996
WO 8102109 A1 8/1981
(Continued)

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.
(Continued)

*Primary Examiner* — Rebecca E Eisenberg
(74) *Attorney, Agent, or Firm* — Standley Law Group LLP; Adam J. Smith

(57) ABSTRACT

An intravascular balloon catheter device includes an outer member disposed about an inner member. A balloon has a proximal portion which is connected to the outer member and a distal portion which is connected to the inner member. A sheath is disposed about the outer member and adapted for movement relative to the balloon. A coating with a therapeutic agent is provided on at least the distal portion of the balloon. The distal portion fits snugly into the sheath so as to provide a substantially watertight engagement therebetween when inside the sheath. The sheath is configured to prevent the proximal portion of the balloon from inflating to a diameter larger than the sheath.

16 Claims, 25 Drawing Sheets

Related U.S. Application Data which is a continuation-in-part of application No. 14/990,477, filed on Jan. 7, 2016, now Pat. No. 10,130,798, and a continuation of application No. PCT/US2014/046616, filed on Jul. 15, 2014.

(60) Provisional application No. 62/102,770, filed on Jan. 13, 2015, provisional application No. 62/012,382, filed on Jun. 15, 2014, provisional application No. 61/846,095, filed on Jul. 15, 2013.

(52) U.S. Cl.
CPC . *A61M 25/1025* (2013.01); *A61M 2025/1004* (2013.01); *A61M 2025/105* (2013.01); *A61M 2025/1056* (2013.01); *A61M 2025/1068* (2013.01); *A61M 2025/1077* (2013.01); *A61M 2025/1079* (2013.01); *A61M 2025/1081* (2013.01); *A61M 2025/1086* (2013.01); *A61M 2205/0222* (2013.01)

(56) References Cited

U.S. PATENT DOCUMENTS

| | | | |
|---|---|---|---|
| 3,704,711 | A | 12/1972 | Park |
| 4,273,128 | A | 6/1981 | Lary |
| 4,292,974 | A | 10/1981 | Fogarty et al. |
| 4,654,027 | A | 3/1987 | Dragan et al. |
| 5,030,201 | A | 7/1991 | Palestrant |
| 5,074,871 | A | 12/1991 | Groshong |
| 5,100,425 | A | 3/1992 | Fischell et al. |
| 5,154,724 | A | 10/1992 | Andrews |
| 5,156,610 | A | 10/1992 | Reger |
| 5,178,625 | A | 1/1993 | Groshong |
| 5,211,651 | A | 5/1993 | Reger et al. |
| 5,224,945 | A | 7/1993 | Pannek, Jr. |
| 5,244,619 | A | 9/1993 | Burnham |
| 5,246,421 | A | 9/1993 | Saab |
| 5,250,060 | A | 10/1993 | Carbo et al. |
| 5,282,484 | A | 2/1994 | Reger |
| 5,318,576 | A | 6/1994 | Plassche, Jr. et al. |
| 5,415,635 | A | 5/1995 | Bagaoisan et al. |
| 5,514,093 | A | 5/1996 | Ellis et al. |
| 5,591,194 | A | 1/1997 | Berthiaume |
| 5,658,309 | A | 8/1997 | Berthiaume et al. |
| 5,665,098 | A | 9/1997 | Kelly et al. |
| 5,676,654 | A | 10/1997 | Ellis et al. |
| 5,697,944 | A | 12/1997 | Lary |
| 5,697,948 | A | 12/1997 | Marin et al. |
| 5,728,067 | A | 3/1998 | Enger |
| 5,728,123 | A | 3/1998 | Lemelson et al. |
| 5,733,296 | A | 3/1998 | Rogers et al. |
| 5,792,158 | A | 8/1998 | Lary |
| 5,800,450 | A | 9/1998 | Lary et al. |
| 5,836,868 | A | 11/1998 | Ressemann et al. |
| 5,876,448 | A | 3/1999 | Thompson et al. |
| 5,961,536 | A | 10/1999 | Mickley et al. |
| 5,968,064 | A | 10/1999 | Selmon et al. |
| 6,071,287 | A | 6/2000 | Verbeek |
| 6,120,515 | A | 9/2000 | Rogers et al. |
| 6,129,708 | A | 10/2000 | Enger |
| 6,165,187 | A | 12/2000 | Reger |
| 6,217,549 | B1 | 4/2001 | Selmon et al. |
| 6,258,108 | B1 | 7/2001 | Lary |
| 6,270,489 | B1 | 8/2001 | Wise et al. |
| 6,283,947 | B1 | 9/2001 | Mirzaee |
| 6,527,740 | B1 | 3/2003 | Jackson et al. |
| 6,599,267 | B1 | 7/2003 | Ray et al. |
| 6,692,466 | B1 | 2/2004 | Chow et al. |
| 6,695,863 | B1 | 2/2004 | Ramzipoor et al. |
| 6,719,773 | B1 | 4/2004 | Boucher et al. |
| 6,884,257 | B1 | 4/2005 | Cox |
| 7,108,704 | B2 | 9/2006 | Trerotola |
| 7,131,981 | B2 | 11/2006 | Appling et al. |
| 7,279,002 | B2 | 10/2007 | Shaw et al. |
| 7,303,572 | B2 | 12/2007 | Melsheimer et al. |
| 7,517,352 | B2 | 4/2009 | Evans et al. |
| 7,686,824 | B2 | 3/2010 | Konstantino et al. |
| 7,691,086 | B2 | 4/2010 | Tkebuchava |
| 7,708,753 | B2 | 5/2010 | Hardert |
| 7,850,685 | B2 | 12/2010 | Kunis et al. |
| 7,850,710 | B2 | 12/2010 | Huss |
| 7,887,557 | B2 | 2/2011 | Kelley et al. |
| 7,955,350 | B2 | 6/2011 | Konstantino et al. |
| 8,323,307 | B2 | 12/2012 | Hardert |
| 8,328,829 | B2 | 12/2012 | Olson |
| 8,348,987 | B2 | 1/2013 | Eaton |
| 8,366,661 | B2 | 2/2013 | Weber et al. |
| 8,398,662 | B2 | 3/2013 | Granada et al. |
| 8,454,636 | B2 | 6/2013 | Konstantino et al. |
| 8,500,789 | B2 | 8/2013 | Wuebbeling et al. |
| 8,685,049 | B2 | 4/2014 | Schur et al. |
| 8,685,050 | B2 | 4/2014 | Schur et al. |
| 8,702,736 | B2 | 4/2014 | Schur et al. |
| 8,740,849 | B1 | 6/2014 | Fischell et al. |
| 8,870,816 | B2 | 10/2014 | Chambers et al. |
| 9,079,000 | B2 | 7/2015 | Hanson et al. |
| 9,192,747 | B2 | 11/2015 | Hardert |
| 9,282,991 | B2 | 3/2016 | Schur et al. |
| 9,364,255 | B2 | 6/2016 | Weber |
| 9,364,284 | B2 | 6/2016 | Groff et al. |
| 9,510,901 | B2 | 12/2016 | Steinke et al. |
| 9,532,798 | B2 | 1/2017 | Schur et al. |
| 9,592,386 | B2 | 3/2017 | Mathur et al. |
| 9,604,036 | B2 | 3/2017 | Burton et al. |
| 10,117,970 | B2 | 11/2018 | Michal et al. |
| 10,314,948 | B2 | 6/2019 | Michal et al. |
| 2001/0007059 | A1 | 7/2001 | Mirzaee |
| 2002/0010489 | A1 | 1/2002 | Grayzel et al. |
| 2002/0143350 | A1 | 10/2002 | Heitzmann et al. |
| 2003/0069547 | A1 | 4/2003 | Gonon |
| 2003/0125756 | A1 | 7/2003 | Shturman et al. |
| 2003/0144677 | A1 | 7/2003 | Lary |
| 2004/0034384 | A1 | 2/2004 | Fukaya |
| 2004/0098014 | A1 | 5/2004 | Flugelman et al. |
| 2004/0122457 | A1 | 6/2004 | Weber |
| 2004/0204738 | A1 | 10/2004 | Weber et al. |
| 2004/0267345 | A1 | 12/2004 | Lorenzo et al. |
| 2005/0055077 | A1 | 3/2005 | Marco et al. |
| 2005/0149102 | A1 | 7/2005 | Radisch, Jr. et al. |
| 2005/0149159 | A1 | 7/2005 | Andreas et al. |
| 2005/0151304 | A1 | 7/2005 | Boelens et al. |
| 2005/0187603 | A1 | 8/2005 | Eidenschink et al. |
| 2005/0240176 | A1 | 10/2005 | Oral et al. |
| 2006/0089637 | A1 | 4/2006 | Werneth et al. |
| 2006/0111736 | A1 | 5/2006 | Kelley |
| 2006/0116701 | A1 | 6/2006 | Crow |
| 2006/0184191 | A1 | 8/2006 | O'Brien |
| 2007/0005093 | A1 | 1/2007 | Cox |
| 2007/0060863 | A1 | 3/2007 | Goeken et al. |
| 2007/0106215 | A1 | 5/2007 | Olsen et al. |
| 2007/0156225 | A1 | 7/2007 | George et al. |
| 2007/0181157 | A1 | 8/2007 | Dadourian |
| 2008/0140051 | A1 | 6/2008 | Bei et al. |
| 2008/0294116 | A1 | 11/2008 | Wolter et al. |
| 2008/0300594 | A1 | 12/2008 | Goto |
| 2008/0300610 | A1 | 12/2008 | Chambers |
| 2009/0099583 | A1 | 4/2009 | Butterfield et al. |
| 2009/0105686 | A1 | 4/2009 | Snow et al. |
| 2009/0192508 | A1 | 7/2009 | Laufer et al. |
| 2009/0204068 | A1 | 8/2009 | Nguyen et al. |
| 2009/0306690 | A1 | 12/2009 | Rivers et al. |
| 2009/0312807 | A1 | 12/2009 | Boudreault et al. |
| 2010/0010521 | A1 | 1/2010 | Kurrus |
| 2010/0121270 | A1 | 5/2010 | Gunday et al. |
| 2010/0168737 | A1 | 7/2010 | Grunewald |
| 2010/0168778 | A1 | 7/2010 | Braido |
| 2010/0330147 | A1 | 12/2010 | Hossainy et al. |
| 2011/0060182 | A1 | 3/2011 | Kassab et al. |
| 2011/0152683 | A1 | 6/2011 | Gerrans et al. |
| 2011/0160645 | A1 | 6/2011 | Sutermeister et al. |
| 2011/0184447 | A1 | 7/2011 | Leibowitz et al. |
| 2011/0288479 | A1 | 11/2011 | Burton |

(56) References Cited

U.S. PATENT DOCUMENTS

| | | | |
|---|---|---|---|
| 2011/0301565 A1* | 12/2011 | Weber | A61M 25/10 604/500 |
| 2012/0053485 A1 | 3/2012 | Bloom | |
| 2012/0143054 A1 | 6/2012 | Eaton et al. | |
| 2012/0157988 A1 | 6/2012 | Stone et al. | |
| 2012/0172901 A1 | 7/2012 | Manderfeld et al. | |
| 2012/0197378 A1 | 8/2012 | Houser | |
| 2013/0066346 A1 | 3/2013 | Pigott | |
| 2013/0131594 A1 | 5/2013 | Bonnette et al. | |
| 2013/0150874 A1 | 6/2013 | Kassab | |
| 2013/0237950 A1 | 9/2013 | Gianotti et al. | |
| 2013/0253467 A1 | 9/2013 | Gianotti et al. | |
| 2014/0277002 A1 | 9/2014 | Grace | |
| 2014/0364896 A1 | 12/2014 | Consigny | |
| 2015/0133978 A1 | 5/2015 | Paul, Jr. | |
| 2016/0354585 A1 | 12/2016 | Pigott | |
| 2017/0056048 A1 | 3/2017 | Erpen | |
| 2017/0238960 A1 | 8/2017 | Hatta et al. | |
| 2018/0264247 A1* | 9/2018 | Mantri | A61M 25/10184 |

FOREIGN PATENT DOCUMENTS

| | | | |
|---|---|---|---|
| WO | 9502370 A2 | 1/1995 | |
| WO | 1996039997 A2 | 12/1996 | |
| WO | 9918862 A1 | 4/1999 | |
| WO | 02078511 A2 | 10/2002 | |
| WO | 02078511 A3 | 10/2002 | |
| WO | 2007095125 A2 | 8/2007 | |
| WO | 2013159066 A1 | 10/2013 | |
| WO | 2014106226 A2 | 7/2014 | |
| WO | 2014/142801 A1 | 9/2014 | |
| WO | 2015190578 A1 | 12/2015 | |
| WO | 2015195606 A1 | 12/2015 | |
| WO | 2016210167 A1 | 12/2016 | |

OTHER PUBLICATIONS

International Search Report of PCT/US12/55079.
Boston Scientific, Rotablator Rotational Atherectomy System, http://www.bostonscientific.com/en-US/products/plaque-modification/rotablator-rotational-atherectomy-system.html, 2017.
Cardinal Health, FLASH Ostial System, Dual balloon angioplasty catheter, Jun. 2016.
Boston Scientific, Sterling 0.018" Balloon Catheter, Jun. 2015.
Ham, S. et al., Safety of Carbon Dioxide Digital Subtraction Angiography, Archives of Surgery, Dec. 2011.
Alexander, J., CO2 Angiography in Lower Extremity Arterial Disease, Endovascular Today, Sep. 2011, pp. 27-34.
Covidien, SpiderFX Embolic Protection Device, 2015, https://www.ev3.net/peripheral/us/embolic-protection/spiderfxtrade-embolic-protection-device.htm.
Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.

* cited by examiner

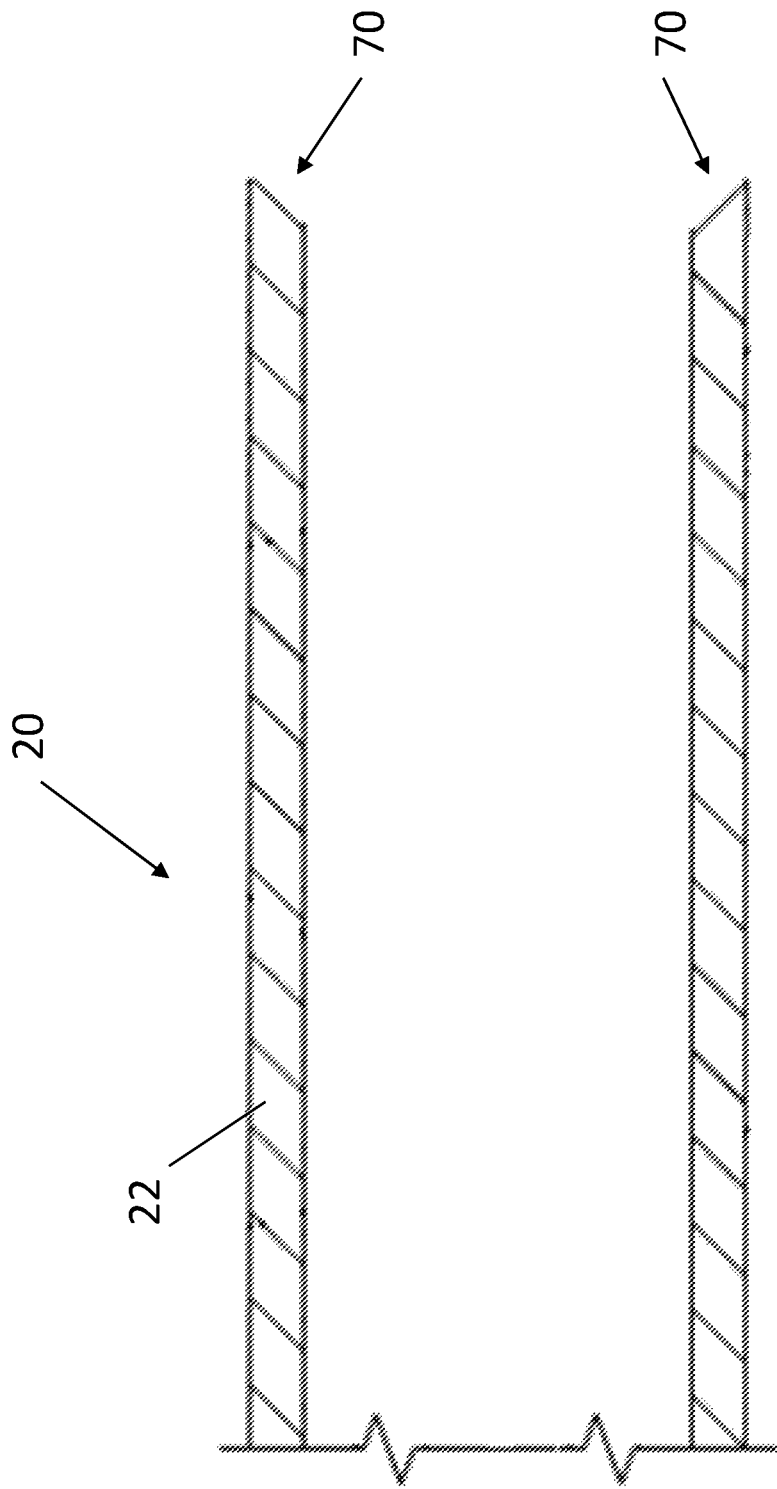

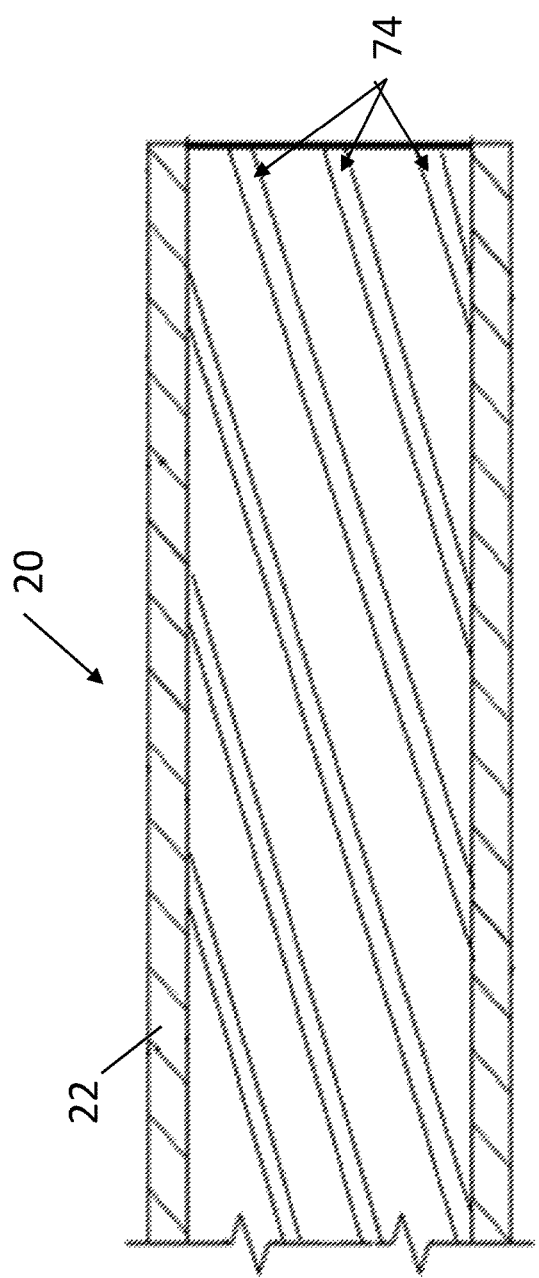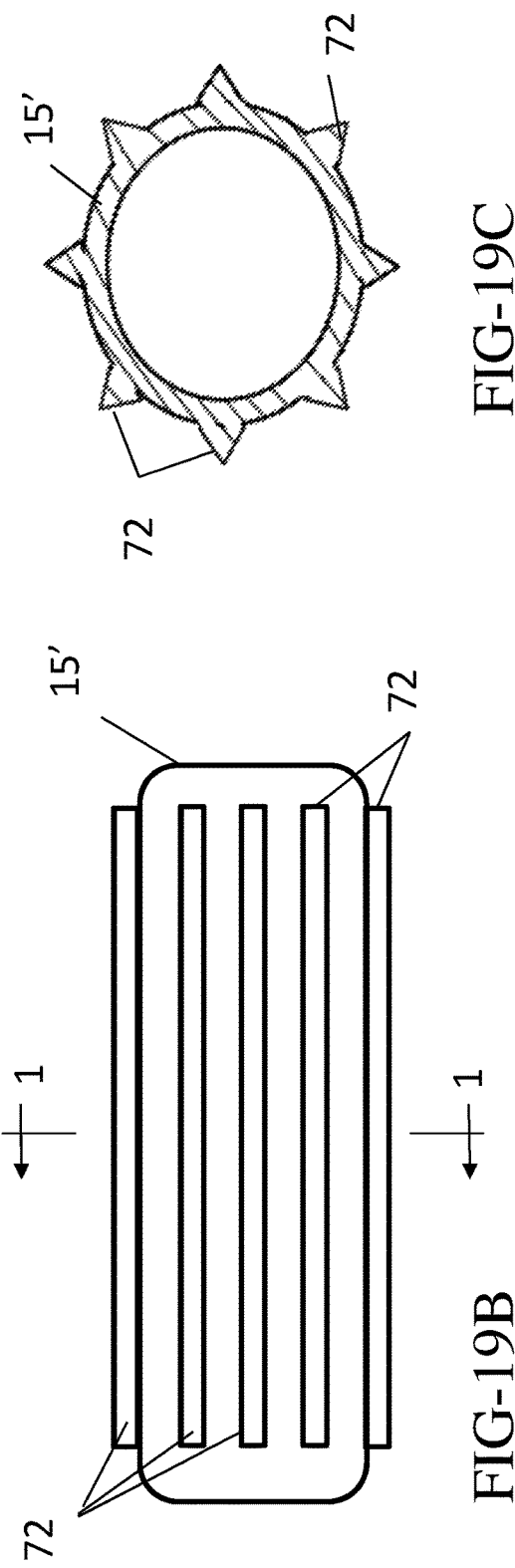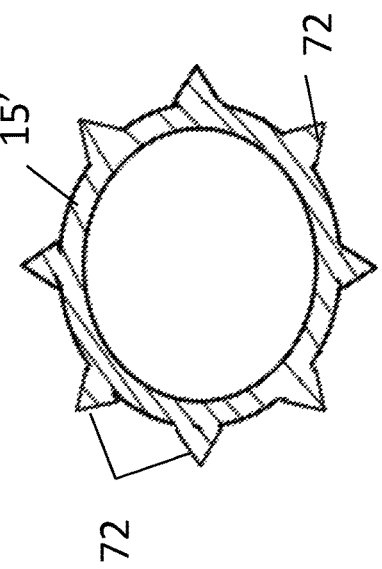

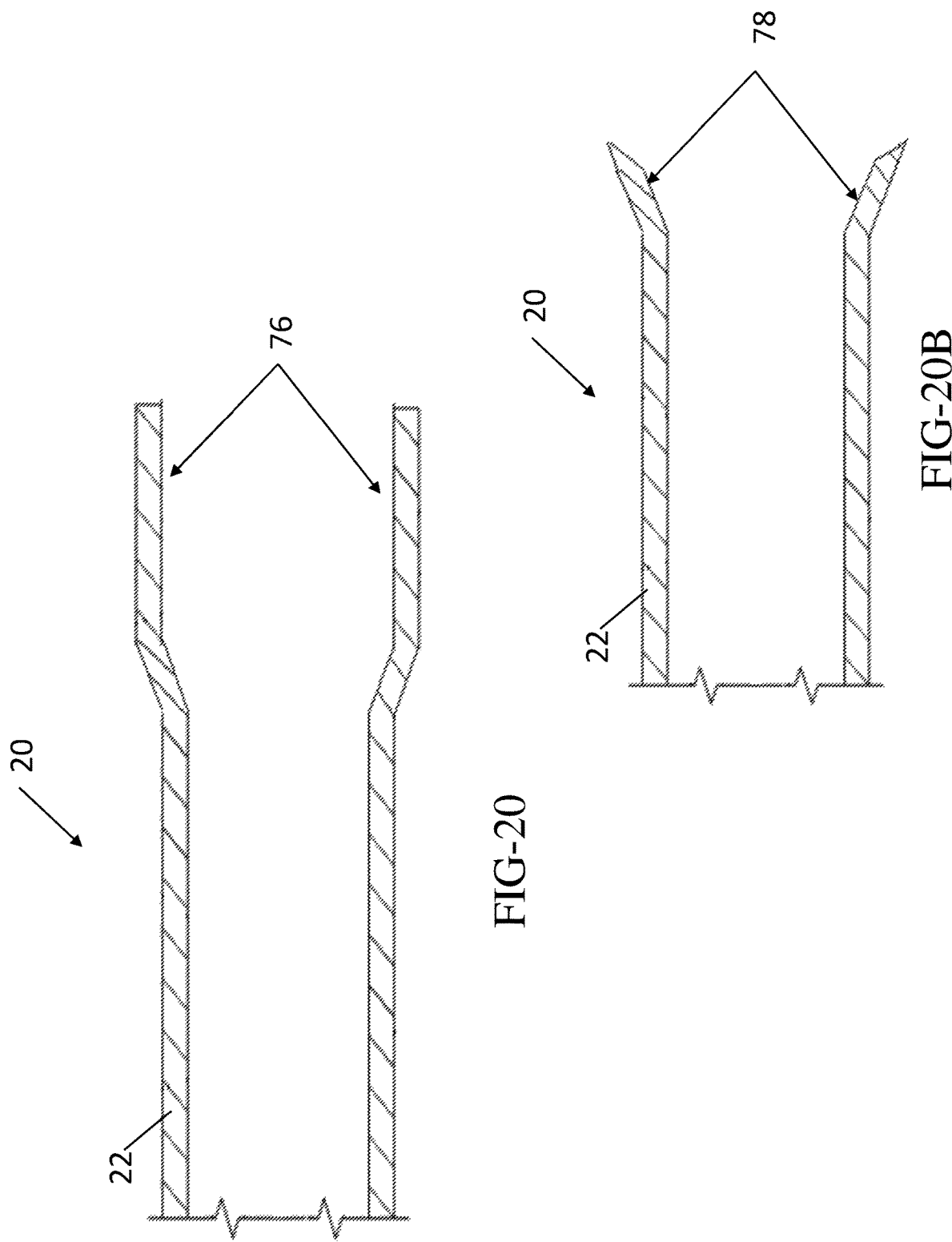

BALLOON CATHETER HAVING A RETRACTABLE SHEATH

CROSS-REFERENCE TO RELATED APPLICATION

This application is a continuation-in-part of U.S. application Ser. No. 15/241,606 filed Aug. 19, 2016, which is a continuation-in-part of U.S. application Ser. No. 14/990,477 filed Jan. 7, 2016, which claims the benefit of U.S. Application No. 62/102,770, filed Jan. 13, 2015, and International Application No. PCT/US2014/046616, filed Jul. 15, 2014, which claims the benefit of U.S. Provisional Application No. 62/012,382, filed Jun. 15, 2014 and U.S. Provisional Application 61/846,095, filed Jul. 15, 2013. The disclosures of all of which are incorporated herein by reference as if restated in their entirety.

TECHNICAL FIELD

Exemplary embodiments of the present invention generally relate to balloon catheters used in surgical procedures.

BACKGROUND AND SUMMARY OF THE INVENTION

This invention relates in general to balloon catheters that are used in surgical procedures. In particular, this invention relates to an improved structure for such a balloon catheter having a retractable sheath that can quickly and easily adjust the length of the inflated portion of the balloon and a locking mechanism for selectively retaining the sheath in the desired position for use.

In many surgical procedures, such as but not limited to percutaneous transluminal angioplasty procedures, a catheter having a selectively inflatable portion provided thereon (commonly referred to as a balloon catheter) is used to open a blockage and/or place a stent in a blood vessel. To accomplish this, a user must select one of various sized balloons to match the blood vessel structure and the length of the treatment area. The balloon of the catheter is initially positioned at a desired zone of attention within the blood vessel. Then, the balloon of the catheter is inflated so as to expand into engagement with an inner surface of the blood vessel, thereby expanding the blockage. If desired, an expandable stent can be disposed about the balloon of the catheter such that when the balloon is inflated, the stent is expanded into engagement with the inner surface of the blood vessel. The balloon and/or the stent is often treated with medication that is delivered by contact with the surface of the blood vessel when the balloon and/or stent is deployed. In either event, the balloon is subsequently deflated after use.

It is important that the balloon be properly sized to the treatment area. If a balloon catheter is too long, the balloon may damage the surrounding tissue. If a balloon is too short, the treatment may be ineffective or require time-consuming repetition. Therefore, care facilities are forced to stock many different size balloon catheters and medical care providers must spend time carefully selecting the properly sized balloon catheter. What is needed is a variable length balloon catheter. Therefore, it would be desirable to provide an improved structure for such a balloon catheter having a retractable sheath that can quickly and easily adjust the length of the portion of the balloon to be inflated and a locking mechanism for selectively retaining said sheath in the desired position for use.

Due to internal pressure, shape, and texture, a partially exposed balloon catheter would have a natural tendency to escape the retractable sheath when inflated. This is much like how a partially protruding watermelon seed has a natural tendency to entirely escape a person's lips, due to the watermelon seed's shape and texture. Here, the same phenomenon applies to a partially exposed balloon catheter from a sheath, though the situation is further complicated by the internal pressure of the balloon. Therefore, it would be desirable to additionally provide a mechanical stop in conjunction with the device where said mechanical stop serves to prevent the balloon from entirely escaping the retractable sheath when the balloon is inflated. Further, the mechanical stop can be used to adjust the effective area of the balloon catheter by controlling the length of the balloon permitted to extend from the sheath.

Recently, medical practitioners have realized that drug coatings may be applied to the outer surface of the intravascular balloons to increase the effectiveness of medical treatment. These so called "drug coated balloons" are exposed to blood and other intravascular fluids upon being inserted into a person's vascular system. This may result in the premature activation, elution, dilution, and loss of the drug coating on the way to the treatment zone. Therefore, it would be desirable to provide a watertight seal between the balloon and the sheath such that the medicated balloon is not exposed to intravascular fluids until the balloon reaches the treatment zone.

The present invention is directed to an improved structure for a balloon catheter having a retractable sheath that can quickly and easily adjust the length of the inflated portion of the balloon and a locking mechanism for selectively retaining the sheath in the desired position for use. The balloon catheter assembly includes an inner member and an outer member that is disposed about the inner member. The outer member includes an inflatable balloon. A sheath is disposed about the outer member for movement relative to the balloon so as to selectively expose some or all of the balloon for inflation. The balloon catheter assembly includes a clamp for selectively securing the sheath at a desired position relative to the balloon. The inner member may comprise a series of indentations or protrusions that engage the clamp such that the user may selectively control the location of the retractable sheath relative to the balloon.

The assembly may further include a mechanical stop that is configured to selectively secure the balloon and prevents it from entirely escaping the sheath when the balloon is inflated. The assembly may comprise a series of graduated markers, such as radiopaque markers, that indicate the position of the balloon relative to the retractable sheath. The balloon may further comprise a strength collar, such as an annulus, located on the distal end of the retractable sheath.

Additionally, the balloon and the sheath may form a substantially watertight engagement with one another. This seal may prevent the medicated coating from being prematurely removed, eluted, or activated prior to the assembly being properly located at the treatment site. In exemplary embodiments of the present invention, the assembly may further comprise a cap that provides a substantially watertight engagement between said cap and the sheath when the balloon is in a retracted position such that the cap abuts the sheath. The balloon may further comprise a lubricious coating between the outer surface of the balloon and the inner surface of the sheath which allows the balloon to move relative to the sheath without disturbing the medicated coating.

It may be advantageous to facilitate incremental adjustments to the exposed portion of the balloon. Additionally, or in the alternative, it may be advantageous to permit recapture and redeployment of the balloon. Balloons are often neatly folded and tightly packed into the smallest possible size sheath because the devices are required to enter and negotiate the patient's oftentimes narrow and winding vascular system. Once the balloon is deployed it is difficult to recover the balloon without wear or damage to the balloon. Regardless, it is also difficult to repackage the balloon in as neat and tidy a manner as it was originally packed. Therefore, what is needed is a variable length balloon having a balloon recapture element to facilitate incremental adjustment and/or protected and efficient repacking of the balloon.

The present invention comprises a variable length balloon with a balloon recapture element that facilitates incremental adjustment to the length of exposed balloon as well as protected and efficient repacking of the balloon. The recapture elements may include rifling along the inner surface of the sheath, a smoothed edge at the distal end of the sheath, a tapered edge at the distal end of the sheath, a funnel-shaped tip at the distal end of the sheath, or some combination thereof. These recapture elements may prevent wear to the balloon during re-sheathing. These recapture elements may also facilitate neat and tidy refolding and repackaging of the balloon in the sheath. Coupled with the variable length nature of the balloon, the recapture elements may facilitate multiple deployments of the balloon at the same or different treatment sites.

Alternatively, or in addition, it may be advantageous to use various balloon sizes and configurations to prevent portions of the balloon from escaping the sheath. For example, without limitation, a proximal portion of the balloon may be more compliant than a distal portion of the balloon. This may permit the proximal portion to inflate against an inner surface of the sheath and secure the relative position of the balloon.

When utilizing such catheter devices, it is sometimes desirable to initially flush the catheter with saline or another liquid to ensure that there is no air present in the catheter device. This is sometimes referred to as "de-airing" the device. Air otherwise in the catheter device could inadvertently be introduced into the patient's vascular system and result in complications. In some cases, it would be advantageous to instead use another biocompatible fluid for flushing the catheter device such as, without limitation, carbon dioxide. Carbon dioxide may be more readily available and cheaper as compared to saline in some situations.

Additionally, sometimes it would be advantageous to use alternative positioning and exchanging systems with the catheter device. For example, a monorail type system might sometimes permit positioning of the catheter device or exchange the current catheter device with another device. Such a system may require a smaller length guidewire as compared to a traditional system.

The present invention may further comprise a balloon having a proximal portion which is relatively compliant as compared to a distal portion. The increased compliance of the proximal portion may permit the proximal portion to expand against the inner wall of the sheath, thereby preventing a portion of the balloon from escaping the sheath. Alternatively, or in addition, the proximal portion may be larger or smaller than the distal portion.

Various aspects of this invention will become apparent to those skilled in the art from the following detailed description of the preferred embodiments, when read in light of the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 18 is an enlarged, side, sectional view of the sheath with the balloon removed to illustrate an exemplary embodiment of a balloon recapture element;

FIG. 19 is an enlarged, side, sectional view similar to FIG. 18 illustrating another exemplary embodiment of the balloon recapture element;

FIG. 19B is a side view of an exemplary pleated balloon for use with the device of FIG. 19, also illustrating section line 1-1;

FIG. 19C is a front, sectional view of the exemplary pleated balloon taken along section line 1-1 of FIG. 19B;

FIG. 20 is an enlarged, side, sectional view similar to FIG. 18 illustrating another exemplary embodiment of the balloon recapture element; and FIG. 20B is an enlarged, side, sectional view similar to FIG. 18 illustrating another exemplary embodiment of the balloon recapture element;

DETAILED DESCRIPTION OF EXEMPLARY EMBODIMENT(S)

Figure 1:
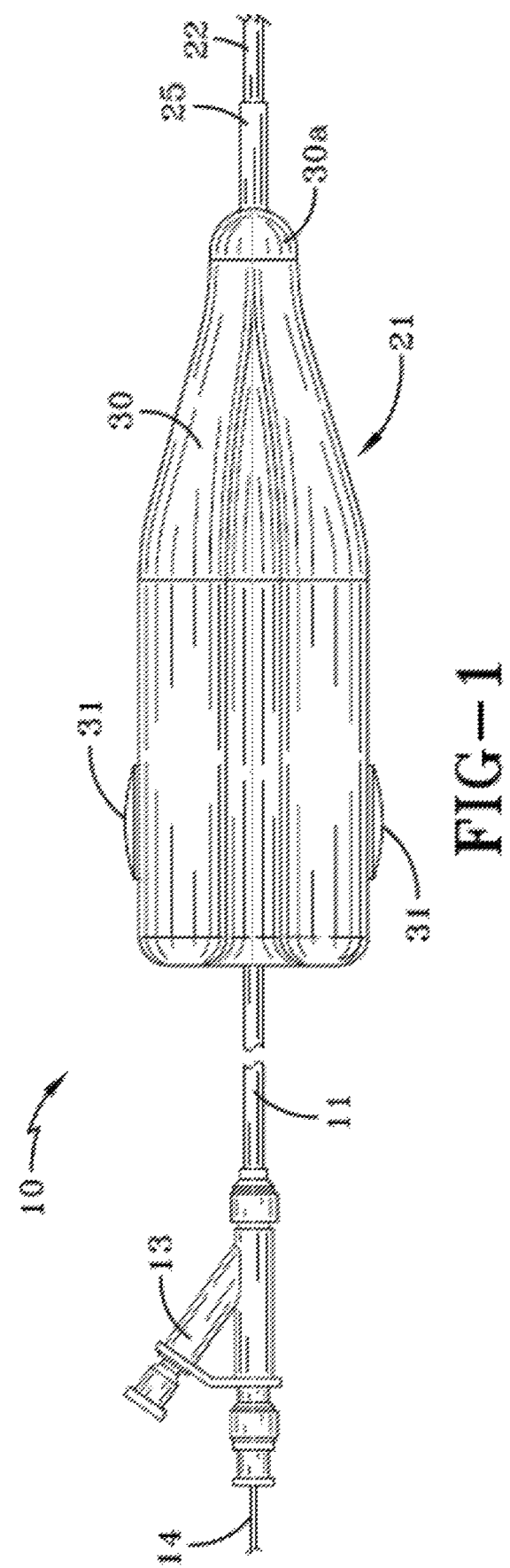
FIG. 1 is a side elevation view of a first end of a balloon catheter assembly.

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
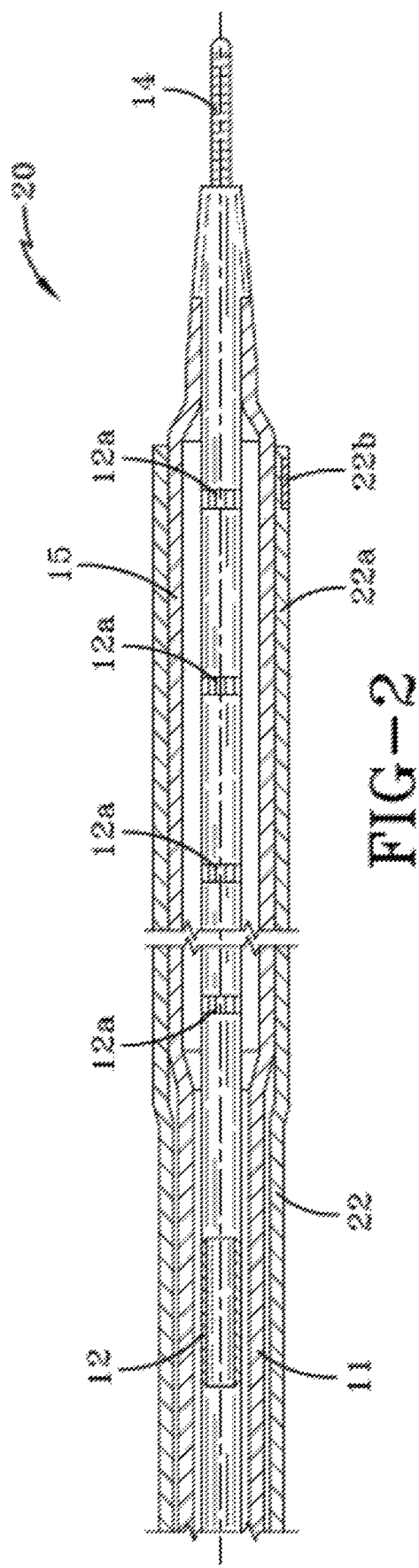
FIG. 2 is an enlarged sectional elevation view of a second end of the balloon catheter assembly illustrated in FIG. 1.

FIG. 1 and FIG. 2 illustrate a balloon catheter assembly, indicated generally at 10. The balloon catheter assembly is comprised of a first end, illustrated in FIG. 1, and a second end, illustrated in FIG. 2. The balloon catheter assembly 10 has an elongated shaft portion that includes an outer member 11 and an inner member 12. The outer member 11 and the inner member 12 may both be tubular in shape, although such is not required. The inner member 12 is disposed within the outer member 11. Thus, an annular outer lumen is defined between the inner surface of the outer tubular member 11 and the outer surface of the inner tubular member 12. Similarly, a cylindrical inner lumen is defined within the inner tubular member 12. The purpose for the outer and inner lumens will be explained below.

In exemplary embodiments of the present invention, one or more radiopaque markers 12a may be provided on the inner tubular member 12. The radiopaque markers 12a are conventional in the art and are provided to facilitate the determination of the location of the inner tubular member 12 during a procedure using conventional fluoroscopy techniques. The radiopaque markers 12a may be spaced in regular intervals. Further, one or more radiopaque markers 22b may be provided on the expanded portion 22a of the sheath 22 to facilitate the determination of the location of the sheath 22 using conventional fluoroscopy techniques during use. The radiopaque markers 12a and 22b may be monitored by the user to determine how far the inner member 12a, and thus the balloon 15, is extended from the sheath 22 thereby permitting the user to monitor how much of the balloon 15 is exposed for treatment of the affected area.

An adapter 13 may be connected to a first end of the elongated shaft portion of the balloon catheter assembly 10. The adapter 13 is conventional in the art and is provided to facilitate access to both the outer and inner lumens during use of the balloon catheter assembly 10. For example, a guide wire 14 can be inserted into the inner lumen via the adapter 13 and through a second end of the elongated shaft portion of the balloon catheter assembly 10, as shown in FIG. 2. The guide wire 14 is conventional in the art and is provided to facilitate the positioning of the balloon catheter assembly 10 at a desired location for use, such as within a blood vessel as described above.

The adapter 13 may comprise a luer lock or similar device configured to facilitate the introduction of a fluid into the balloon catheter assembly 10. The fluid may be used to flush the balloon catheter assembly 10 prior to use. For example, without limitation, the fluid may be used to remove any air from the balloon catheter assembly 10 prior to inserting any portion of the balloon catheter assembly 10 into the patient's vascular system. The fluid may be any kind of biocompatible fluid including, but not limited to, saline, carbon dioxide, and the like. In exemplary embodiments, the luer lock and/or the adapter 13 may be configured to accept a carbon dioxide cartridge for flushing the balloon catheter assembly 10.

The outer tubular member 11 includes an inflatable balloon 15. The balloon 15 is conventional in the art and may be connected to the outer tubular member 11 such that at least a portion of the inflatable balloon 15 extends about an end portion of the inner tubular member 12. The interior of the balloon 15 communicates with the outer lumen of the balloon catheter assembly 10. As a result, an inflation fluid can be selectively introduced into the adapter 13 and through the outer lumen to the interior of the balloon 15, causing it to inflate in a known manner. Additionally, the interior of the balloon 15 can be vented through the outer lumen and the adapter 13 to the atmosphere, allowing it to deflate after use.

The balloon catheter assembly 10 includes an adjustable sheath assembly, indicated generally at 20. As be explained in detail below, the adjustable sheath assembly 20 is provided to selectively define a portion of the balloon 15 that is desired to be inflated during use. To accomplish this, the balloon catheter assembly 10 includes a clamp, indicated generally at 21, and a sheath 22. The clamp 21 is disposed about the outer member 11 adjacent to the adapter 13 and the first end of the elongated shaft portion of the balloon catheter assembly 10. The structure and operation of the clamp 21 will be explained in detail below.

The sheath 22 may extend from the clamp 21 about the outer member 11 toward the second end of the elongated shaft portion of the balloon catheter assembly 10. In the illustrated embodiment, the sheath 22 includes an expanded portion 22a that is located adjacent to the second end of the elongated shaft portion of the balloon catheter assembly 10. One or more optional radiopaque markers 22b may be provided on the expanded portion 22a of the sheath 22 to facilitate the determination of the location of the sheath 22 using conventional fluoroscopy techniques during use. Also, the expanded portion 22a of the sheath 22 may have an elastically expandable distal tip provided thereon that is expanded in a conventional manner when the balloon 15 is inflated. The structure and operation of the optional elastically expandable distal tip will be explained in detail below.

Treatments to various size vascular zones of attention may be provided utilizing the present invention. To perform such treatments, a user may first provide an intravascular catheter device consistent with the present invention. Next, the user may direct the catheter to a pre-determined zone of attention within a person's vascular system. Then the user may move the sheath relative to the balloon so to selectively expose a portion of the balloon for inflation. The user may next temporarily secure the sheath relative to the balloon. The user may then inflate the balloon. In exemplary embodiments of the present invention, these steps may include providing a medical treatment device, such as but not limited to a stent, in conjunction with the present invention. The medical treatment device may be deployed when the balloon is inflated, or it may be deployed as another step. In either case, the balloon may then be deflated and removed.

The present invention may also provide a method for minimizing or all together eliminating premature activation, elution, dilution, or removal of a drug coating on the balloon and the medical treatment device. To do so, first the user may provide an intravascular catheter device consistent with the present invention. Next, the user may direct the catheter to the pre-determined zone of attention within the person's vascular system. Then the user may move the sheath relative to the balloon so to selectively expose a portion of the drug coated balloon or the medical treatment device for activation. The balloon may be inflated to place the outer surface of the balloon and the medical treatment device in contact with the surrounding blood vessel wall. The balloon may be deflated and removed. It is notable that while the aforementioned method is described with the medical treatment device, such is not required.

Figure 3:
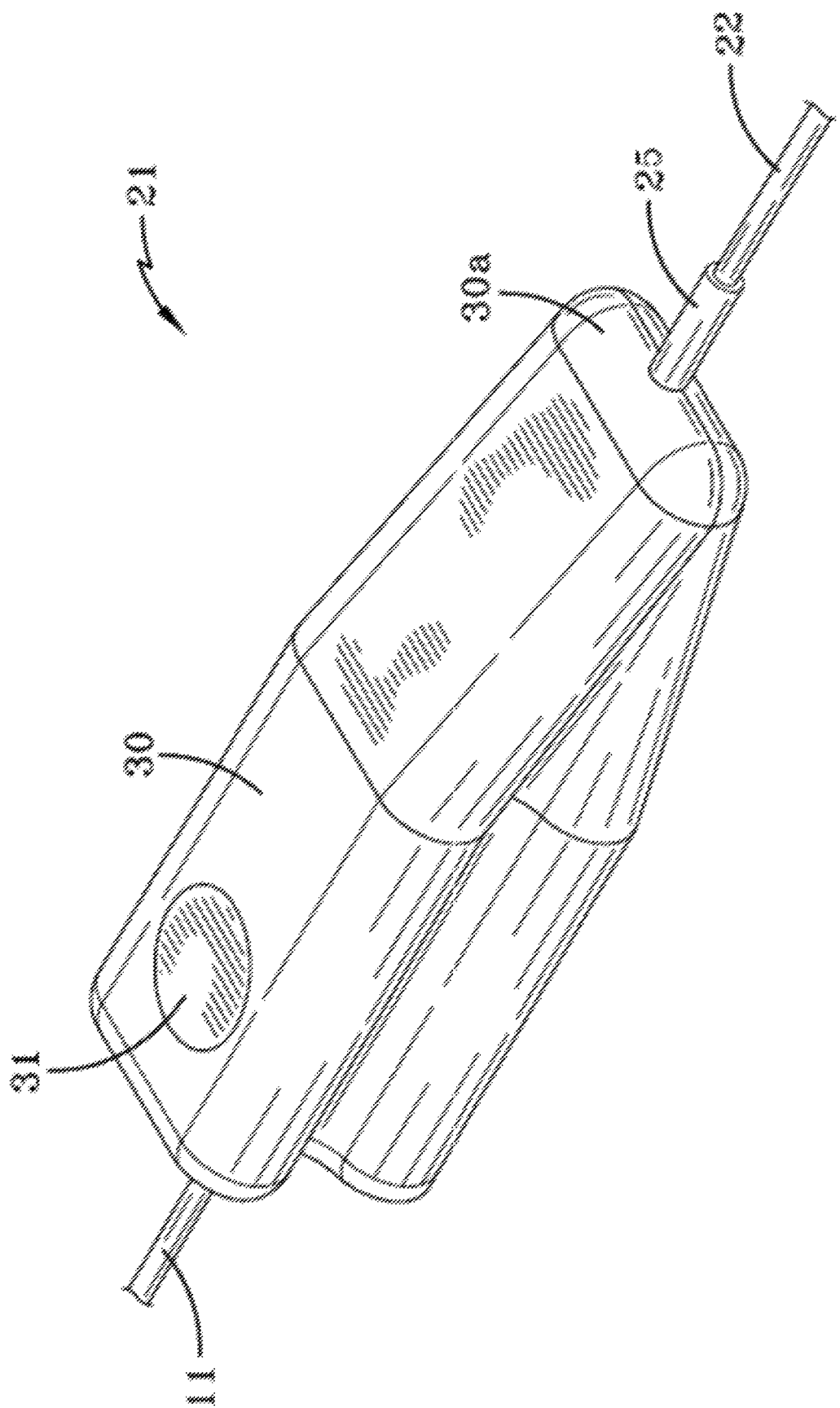
FIG. 3 is a perspective view of a clamp of the balloon catheter assembly illustrated in FIG. 1.

FIG. 3 illustrates the external structure of an exemplary embodiment of the clamp 21. As further illustrated in FIG. 4 and FIG. 5, the clamp 21 includes a housing 30 through which the outer member 11 of the elongated shaft portion of the balloon catheter assembly 10 extends. The housing 30 includes a push button 31 and a tip 30a. The tip 30a may include a protective member 25 that permits the passage of the sheath 22. In exemplary embodiments of the present invention, the sheath 22 is connected directly to the tip 30a. Thus, the housing 30 of the clamp 21 is connected to the sheath 22 for movement therewith, as will be explained in detail below.

Figure 4:
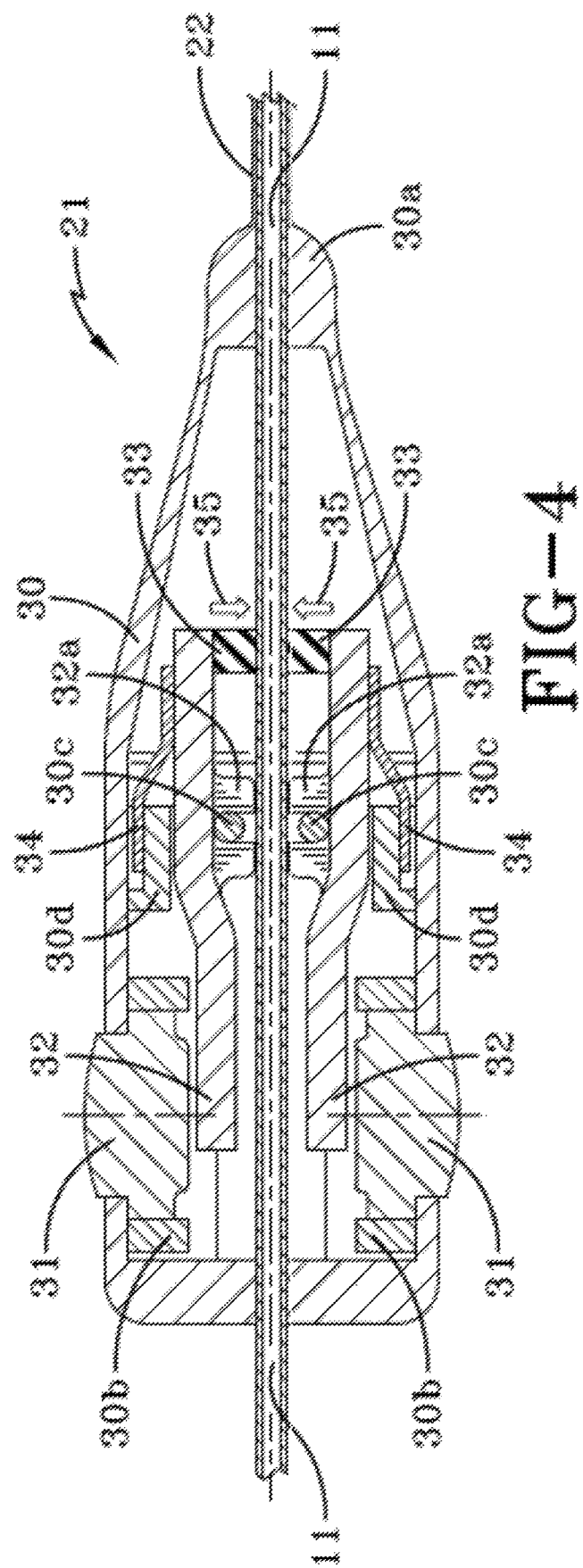
FIG. 4 is an enlarged sectional elevation view showing the clamp of the balloon catheter assembly illustrated in FIG. 1 in a locked condition.
Figure 5:
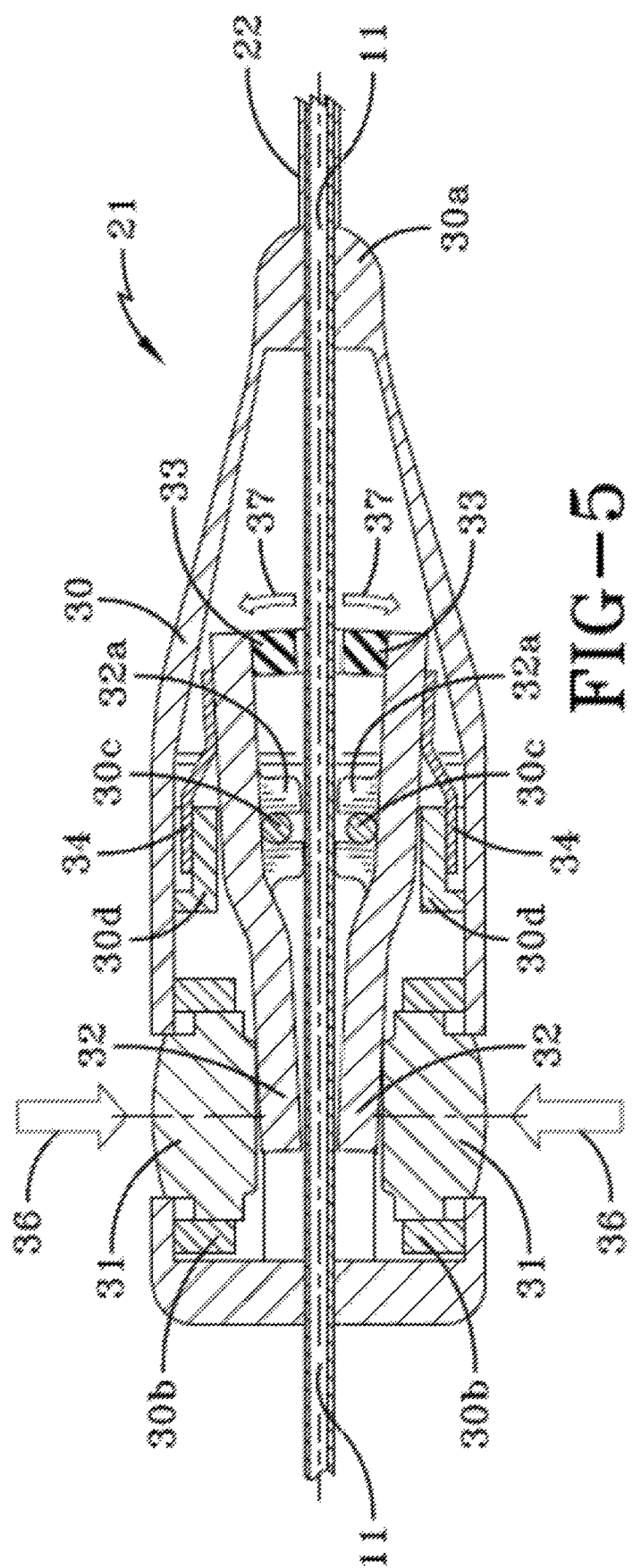
FIG. 5 is an enlarged sectional elevation view similar to FIG. 4 showing the clamp of the balloon catheter assembly in an unlocked condition.

FIG. 4 and FIG. 5 illustrate the internal structure of an embodiment of the clamp 21. The housing 30 of the clamp 21 also includes a pair of button supports 30b, within which respective manually operable push buttons 31 are supported for inward and outward movement relative to the housing 30. In the illustrated embodiment, each of the button supports 30b is generally hollow and cylindrical in shape, and each of the push buttons 31 is generally cylindrical in shape. However, the button supports 30b and the push buttons 31 may have any desired shape or combination of shapes. The purpose for the push buttons 31 will be explained below.

The housing 30 of the clamp 21 further includes a pair of actuator arm supports 30c, upon which respective actuator arms 32 are supported for pivoting movement relative to the housing 30. In the illustrated embodiment, each of the actuator arm supports 30c is a generally cylindrical protrusion that extends inwardly within the housing 30. However, the actuator arm supports 30c may have any desired shape or combination of shapes. Each of the illustrated actuator arms 32 is provided with a pair of legs 32a that define a pocket. The actuator arm supports 30c of the actuator arms 32 are respectively received within the pockets defined by the pairs of legs 32a of the actuator arms 32. Thus, as will be explained in detail below, the actuator arms 32 are respectively supported on the actuator arm supports 30c of the housing 30 for independent pivoting movement relative thereto.

The first ends of the actuator arms 32 are respectively disposed adjacent to the inner ends of the push buttons 31. The actuator arms 32 also include respective second ends that are disposed remotely from the first ends. In the illustrated embodiment, respective engagement pads 33 are secured to the inner surfaces of the second ends of the actuator arms 32. The engagement pads 33 may be formed from any desired material or combination of materials and may, if desired, be omitted entirely. However, it is preferred that the engagements pads 33 be formed from a material having a relatively high coefficient of friction, such as rubber. The purpose for the engagement pads 33 will be explained below.

Lastly, the housing 30 of the clamp 21 may include a pair of springs 34 that independently bias the two actuator arms 32 toward each other. In the illustrated embodiment, each of the springs 34 is formed from a flat piece of resilient material, such as a metallic material, that has been deformed to achieve a desired shape and bias. However, the springs 34 may be formed from any desired material or combination of materials and take any shape. The springs 34 may have first ends that are received within respective spring supports 30d provided on the inner surface of the housing 30. The springs 34 also may have second ends that bear inwardly upon respective outer surfaces of the second ends of the actuator arms 32. The purpose for the springs 34 will be explained below.

FIG. 4 illustrates the clamp 21 of the balloon catheter assembly 10 in a locked condition. In this locked condition, the second ends of the springs 34 bear inwardly upon respective outer surfaces of the second ends of the actuator arms 32. As a result, the engagements pads 33 are urged inwardly toward one another, as shown at 35, so as to engage and may exert a force on opposed portions of the outer surface of the outer member 11 of the balloon catheter assembly 10, which extends through the interior of the housing 30 of the clamp 21. As mentioned above, the engagements pads 33 are preferably formed from a material having a relatively high coefficient of friction. Thus, when the clamp 21 of the balloon catheter assembly 10 is in the locked condition, the outer member 11 of the balloon catheter assembly 10 is hindered or wholly prevented from moving axially relative to the housing 30 of the clamp 21. As mentioned above, the housing 30 of the clamp 21 is connected at the tip 30a to the sheath 22 for movement therewith. Accordingly, when the clamp 21 of the balloon catheter assembly 10 is in the locked condition, the outer member 11 of the balloon catheter assembly 10 is also prevented from moving axially relative to the sheath 22.

FIG. 5 illustrates the clamp 21 of the balloon catheter assembly 10 in an unlocked condition. To achieve this unlocked condition, a user of the balloon catheter assembly 10 may apply inwardly directed forces, as shown at 36, against the manually operable push buttons 31. These forces overcome the forces exerted by the springs 34 and cause the actuator arms 32 to pivot such that the engagements pads 33 are moved out of engagement, as shown at 37, with the opposed portions of the outer surface of the outer member 11 of the balloon catheter assembly 10. Thus, when the clamp 21 of the balloon catheter assembly 10 is in the unlocked condition, the outer member 11 of the balloon catheter assembly 10 is permitted to move axially relative to the housing 30 of the clamp 21. As mentioned above, as the housing 30 of the clamp 21 may be connected at the tip 30a to the sheath 22 for movement therewith, when the clamp 21 of the balloon catheter assembly 10 is in the unlocked condition, the outer member 11 of the balloon catheter assembly 10 is also permitted to move axially relative to the sheath 22.

Although this invention has been described in the context of the illustrated clamp 21, it will be appreciated that this invention may be practiced with any other desired structure for preventing the balloon 15 from slipping in relation to the sheath 22. For example, a variety of known structures may be used for this purpose. Some of such known structures include a duckbill pinch, a spring-activated clamp, a screw mechanism onto catheter, a Tuohy-Borst type of valve, and the like. Furthermore, it is possible to practice this invention without any clamp 21.

Figure 6:
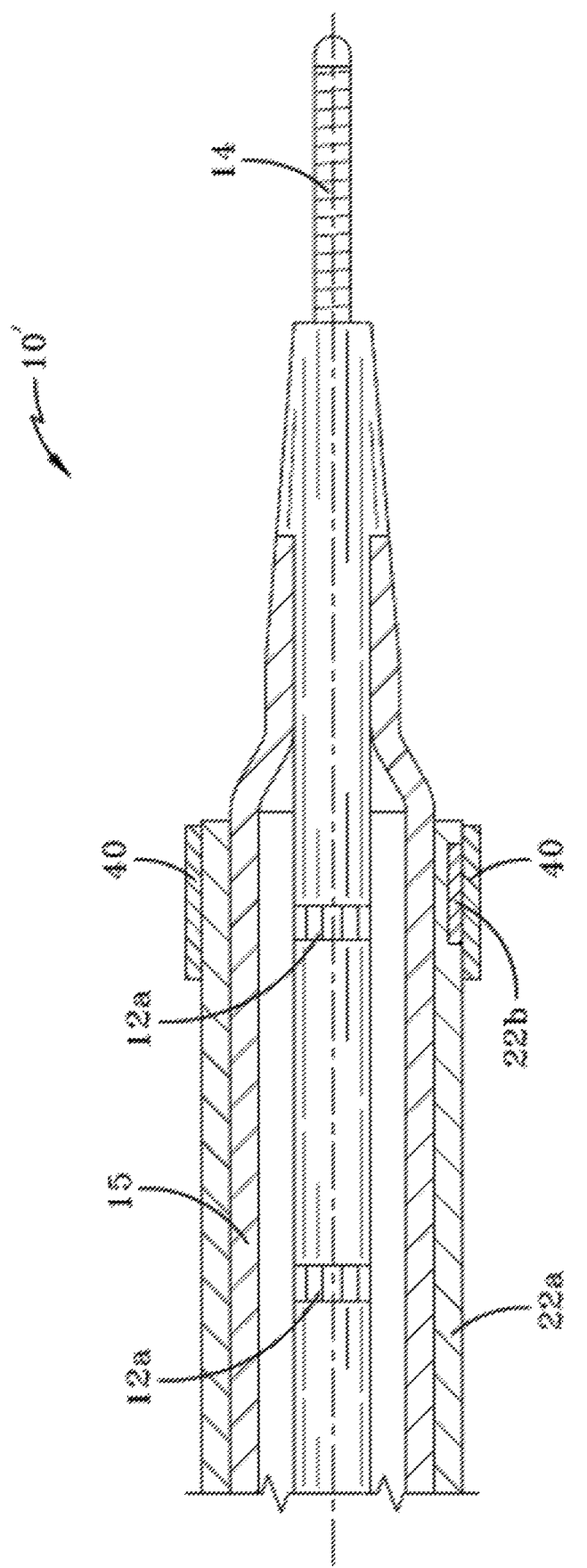
FIG. 6 is a further enlarged sectional elevation view of a second end of a balloon catheter assembly.

FIG. 6 illustrates a second end of the balloon catheter assembly, indicated generally at 10', in accordance with this invention. Like reference numbers are used to indicate components that are the same as described above. As shown therein, the second end of the modified balloon catheter assembly 10' has a collar 40 provided thereon. The purpose of the collar 40 is to prevent the sheath 22 from splitting or otherwise being deformed or damaged as a result of the pressure force exerted by the balloon 15 when it is inflated. The illustrated collar 40 is tubular in shape and extends completely about the end of the sheath 22 where the balloon 15 is located. However, it will be appreciated that the collar 40 may have any desired shape and may be located at any desired position on the sheath 22 or cover any desired portion of the sheath 22. The collar 40 may be formed from any desired material, such as a metallic material, a high strength aramid fiber material (such as is commercially available under the Kevlar® brand name), a high durometer plastic material, or the like. If desired, the collar 40 may be formed from a radiopaque material, allowing it to function as a marker for the distal tip of the sheath 22. If desired, the distal tip of the sheath 22 may be provided with a smooth edge (not shown) so as not to present a sharp edge toward the balloon 15.

The tip of the balloon 15 may fit snugly into the end of the sheath 22 so as to provide a watertight engagement therebetween. Such a watertight engagement would maintain the integrity of the interior compartment of the balloon catheter assembly 10 during its insertion within a blood vessel or other portion of a body and during travel to the treatment site. This may be utilized to maintain a dry interior. Maintaining the interior compartment of the balloon catheter assembly 10 dry facilitates the use of conventional drug-coated balloons, stents, and other devices. The coatings provided on such devices are, in some instances, activated by contact with blood and water. In known catheter assemblies, a significant amount of the drugs provided on the balloons, stents, and other devices can be eluted during the initial insertion of the catheter assembly through blood vessels having flowing blood. The watertight engagement of this invention allows for minimal elution of the drugs during the initial insertion of the balloon catheter assembly 10 and maximal delivery of the drugs to the desired site. As will be explained in greater detail in subsequent figures, a sealed engagement may alternatively be obtained by the use of a tapered insertion tip 60. A lubricious coating may be provided between the sheath 22 and the outer surface of the balloon 15, such that the lubricious coating may reduce or eliminate disturbance to the drug coating when the balloon 15 is moved relative to the sheath 22.

The sheath 22 may protect the various components of the adjustable sheath assembly 20 when moving through the persons' vascular system. The sheath 22 may also protect any drug coating provided on the outer surface of the balloon 15 from being prematurely scraped off, eluted, or activated such as, without limitation, by contact with the persons' bodily fluids or vascular structures. Furthermore, the sheath 22 may protect the adjustable sheath assembly 20 and/or any drug coating provided on the balloon 15 from contact with the procedural sheath that may be used over the adjustable sheath assembly 20. The sheath 22 may also protect the adjustable sheath assembly 20 and/or any drug coating provided on the balloon 15 from contact with vascular walls of the person, particularly when navigating sinuous or narrow passages. The sheath 22 may also protect the adjustable sheath assembly 20 and/or any drug coating provided on the balloon 15 from contact with other objects in the persons' vascular system, such as but not limited to, blockages. While the sheath 22 is described as protecting the components of the adjustable sheath assembly 20, it should be appreciated that the sheath 22 may similarly protect the persons' vascular system from the various components of the adjustable sheath assembly 20.

Figure 7:
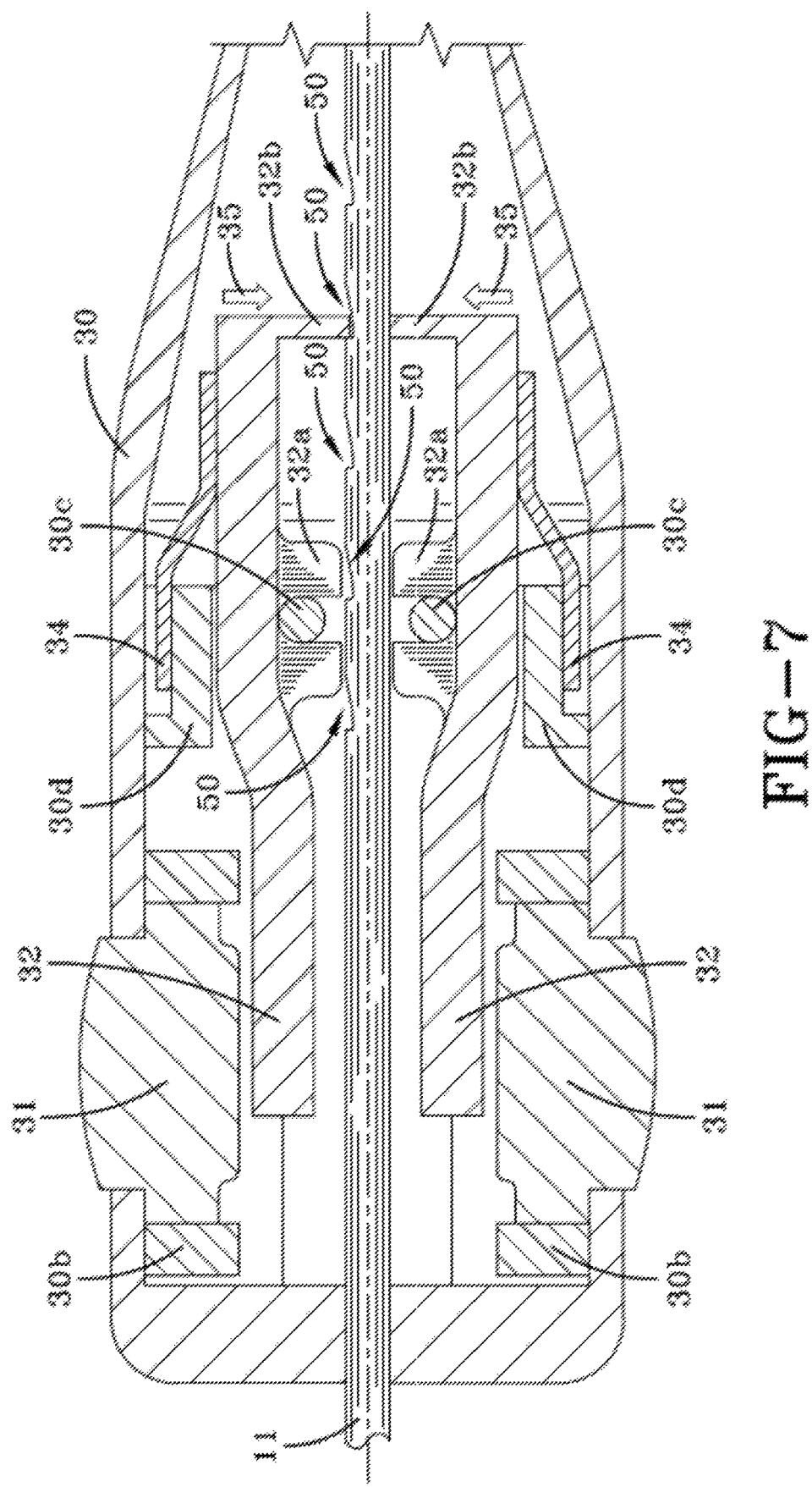
FIG. 7 is an enlarged sectional elevation view similar to FIG. 4, wherein a series of spaced indentations/protrusions are provided on one side of the movable sheath.

FIG. 7 illustrates one side of the outer member 11 provided with a plurality of spaced indentations or protrusions, indicated generally at 50. The indentations or protrusions 50 may have any desired shape or size (or combination of shapes and sizes) and may be provided at any desired location(s) on the one side of the outer member 11. Any number of indentations or protrusions 50 is contemplated. The indentations or protrusions 50 are adapted to cooperate with one or more inwardly extending portions 32b provided on either or both of the actuator arms 32. Thus, when the clamp 21 of the balloon catheter assembly 10 is in the locked condition, the inwardly extending portions 32b provided on either or both of the actuator arms 32 engage one or more of the indentations or protrusions 50. As a result, the outer member 11 of the balloon catheter assembly 10 is prevented from moving axially relative to the housing 30 of the clamp 21. Conversely, when the clamp 21 of the balloon catheter assembly 10 is in the unlocked condition, the inwardly extending portions 32b provided on either or both of the actuator arms 32 do not engage one or more of the indentations or protrusions 50. As a result, the outer member 11 of the balloon catheter assembly 10 is permitted to move axially relative to the housing 30 of the clamp 21.

Figure 8:
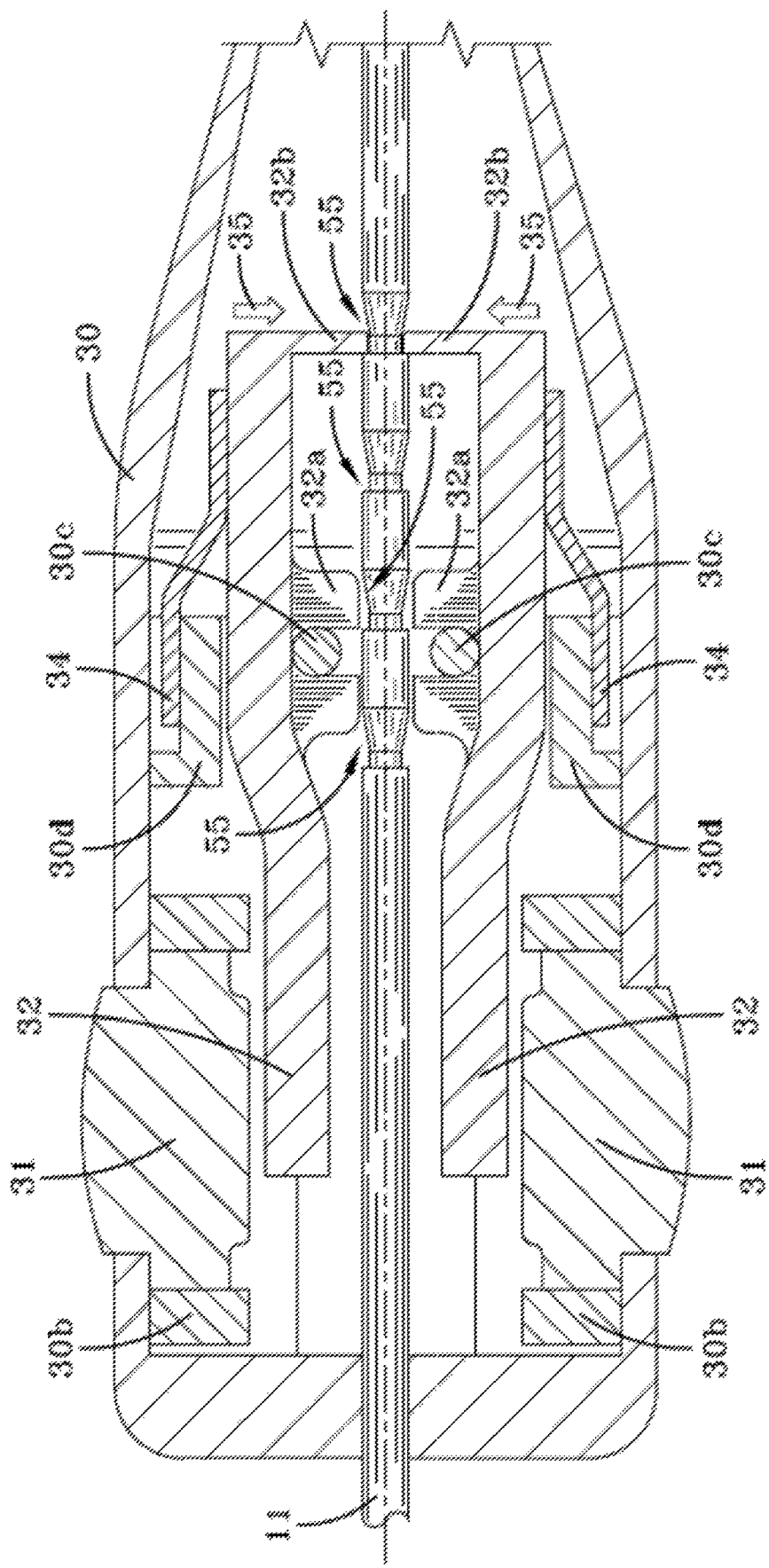
FIG. 8 is an enlarged sectional elevation view similar to FIG. 7, wherein a series of annular spaced indentations/protrusions are provided about the circumference of the movable sheath.

FIG. 8 illustrates a series of annular spaced indentations or protrusions, indicated generally at 55. The indentations or protrusions 55 may have any desired shape or size (or combination of shapes and sizes) and may be provided at any desired location(s) on the outer member 11. Any number of indentations or protrusions 55 is contemplated. The indentations or protrusions 55 are adapted to cooperate with one or more of the inwardly extending portions 32b provided on either or both of the actuator arms 32. Thus, when the clamp 21 of the balloon catheter assembly 10 is in the locked condition, the inwardly extending portions 32b provided on either or both of the actuator arms 32 engage one or more of the indentations or protrusions 55. As a result, the outer member 11 of the balloon catheter assembly 10 is prevented from moving axially relative to the housing 30 of the clamp 21. Conversely, when the clamp 21 of the balloon catheter assembly 10 is in the unlocked condition, the inwardly extending portions 32b provided on either or both of the actuator arms 32 do not engage one or more of the indentations or protrusions 55. As a result, the outer member 11 of the balloon catheter assembly 10 is permitted to move axially relative to the housing 30 of the clamp 21.

The annular spaced indentations or protrusions 55 may be a series of identical annular spaced indentations or protrusions 55. Each section of the annular spaced indentations or protrusions 55 may be defined by a tubular section with an outer diameter smaller than the outer diameter of the outer member 11, a conical section with an initial outer diameter equal to the smaller outer diameter of the previous section, transitioning to an outer diameter substantially equal to the outer diameter of the outer member 11, and finally, a second tubular section with an outer diameter substantially equal to the outer diameter of the outer member. This design allows for the inwardly extending portions 32b to ratchet as each section of the annular spaced indentation or protrusion 55 passes the inwardly extending portions 32b. This may provide the user with tactile and audible feedback as each section passes through the inwardly extending portion 32b. In the illustrated embodiment this would prevent the clamp 21 from moving distally relative to the balloon catheter assembly 10. It is contemplated that the annular spaced indentations or protrusions 55 may be reversed such that the indentations or protrusions 55 prevent the clamp 21 from moving proximally relative to the balloon catheter assembly 10.

Figure 9:
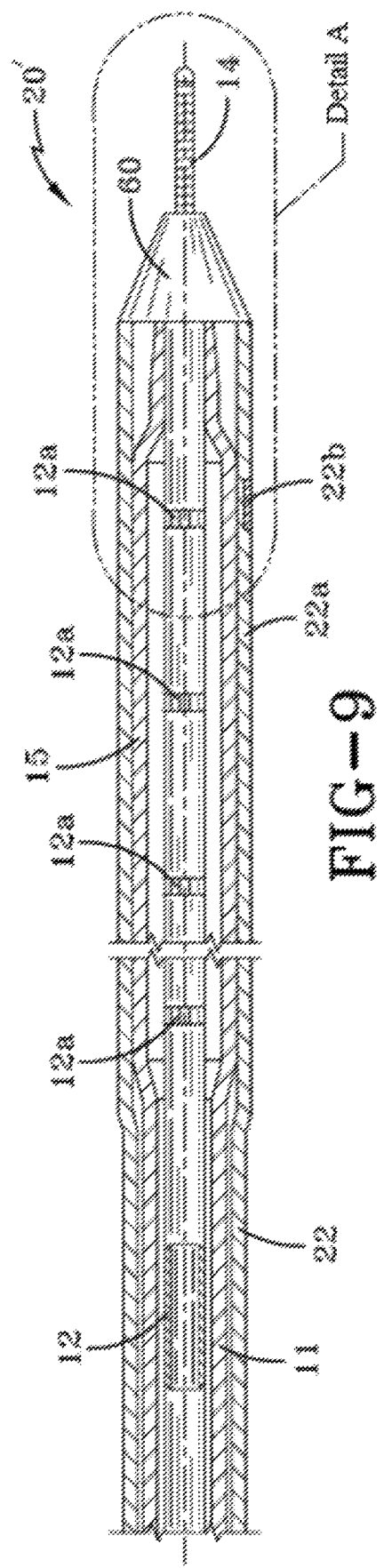
FIG. 9 is a sectional elevation view similar to FIG. 2 showing the end of the sheath in sealing engagement with a tapered insertion tip and indicating Detail A.
Figure 10:
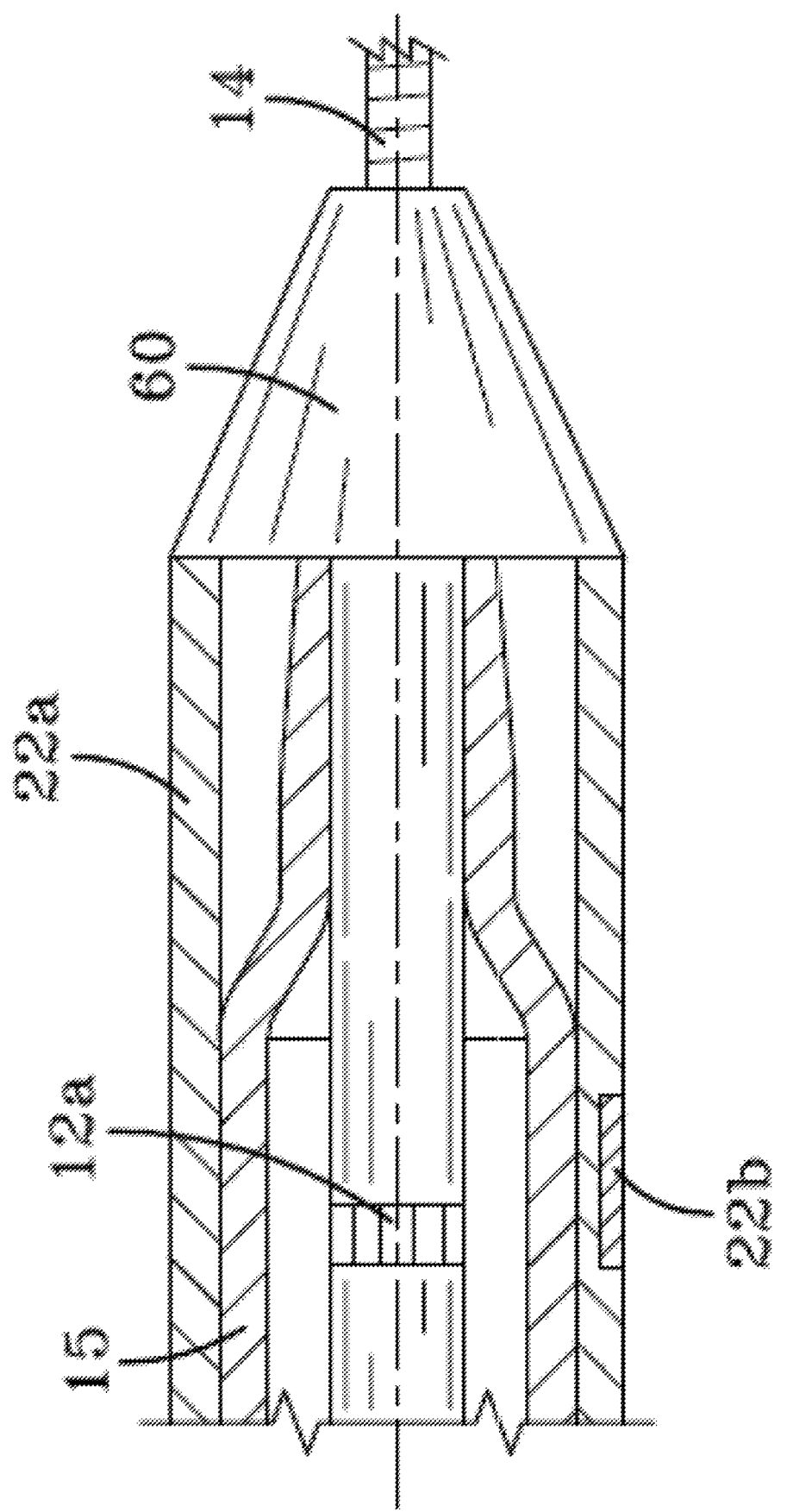
FIG. 10 is an enlarged view of the tapered insertion tip illustrated in Detail A of FIG. 9.
Figure 11:
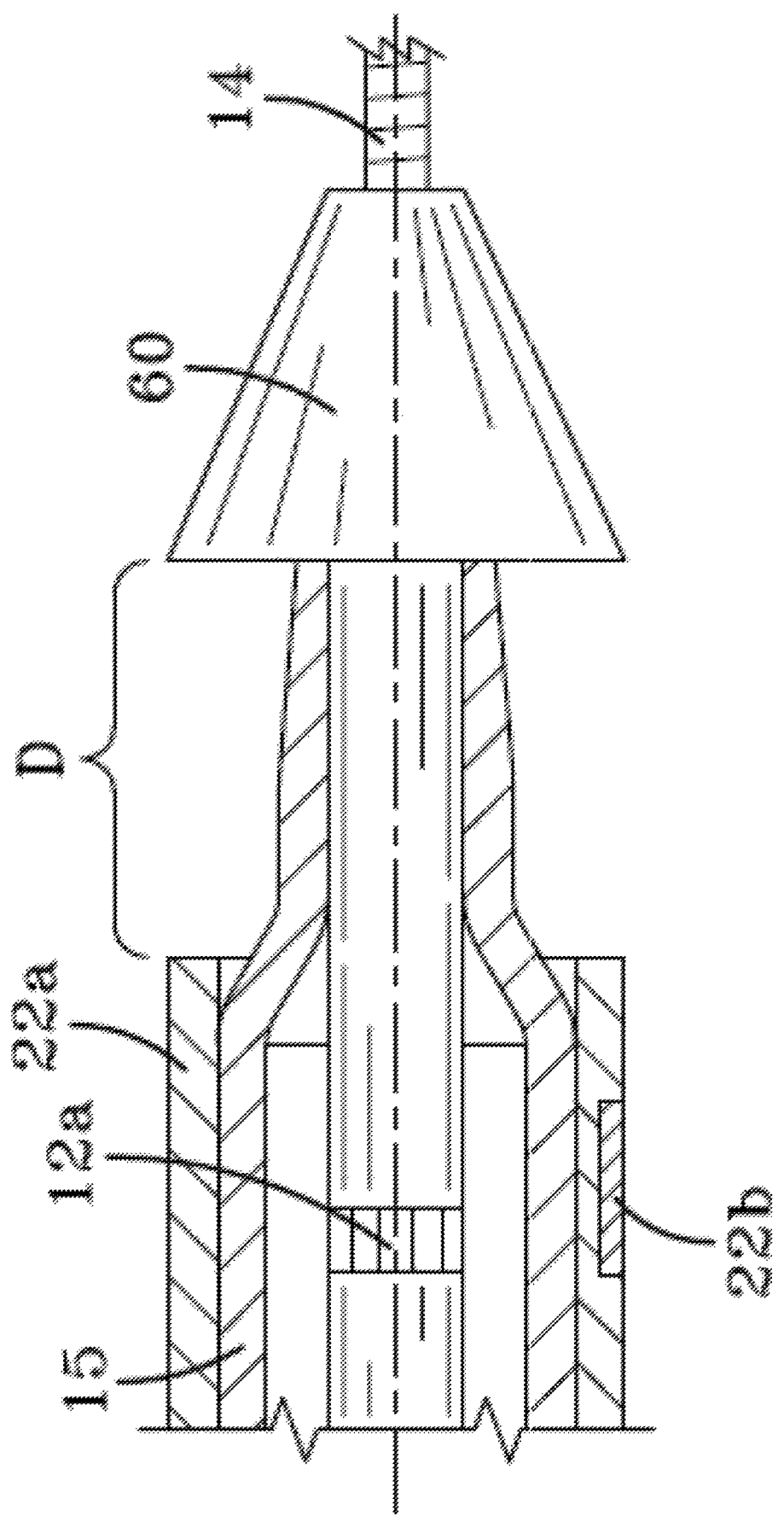
FIG. 11 is an enlarged view similar to FIG. 10 showing the sheath partially retracted to expose the balloon.

FIG. 9, FIG. 10, and FIG. 11 illustrate a modified end of the adjustable sheath assembly 20' with the tapered insertion tip 60. In FIG. 9 and FIG. 10, the end of the adjustable sheath assembly 20' is in sealing engagement with the tapered insertion tip 60. FIG. 11 is similar to FIG. 10 but shows the end of the adjustable sheath assembly 20' partially retracted to expose the balloon 15 in the manner described above. One or more radiopaque markers (not shown) may be placed on the tapered insertion tip 60 and monitored using conventional fluoroscopy techniques such that the user may determine the distance, shown in FIG. 11 as "D", between the sheath 22a and the tapered insertion tip 60. This also permits the user to determine the exposed length of the balloon 15.

The sheath 22 and tapered insertion tip 60 may protect the drug coating or drug coated devices such that the drug coating is not activated, eluted, diluted, or removed when the balloon catheter assembly 10 is placed into the blood vessel. In exemplary embodiments of the present invention, the balloon 15 alone may provide a sealing engagement with the sheath 22. The balloon catheter assembly 10 may additionally comprise a lubricious coating provided between the sheath 22 and the balloon 15 to facilitate the movement of the balloon 15 relative to the sheath 22 by reducing or eliminating disturbance to the drug coating. In exemplary embodiments of the present invention, the lubricious coating may additionally or alternatively be combined with or placed over the top of the medicated coating.

Figure 12:
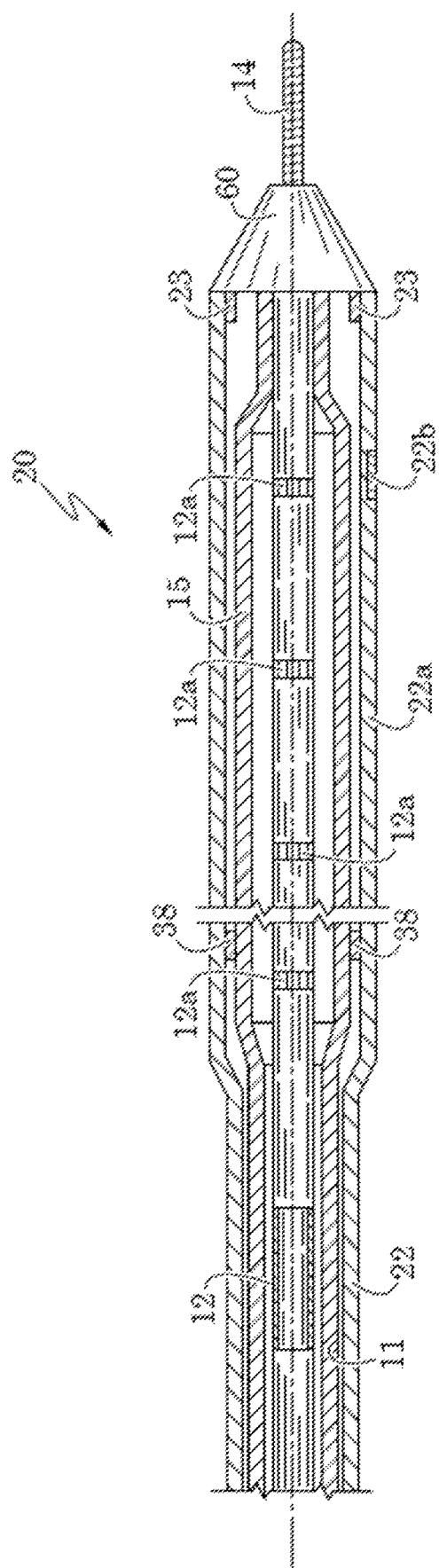
FIG. 12 is a sectional elevation view similar to FIG. 9 showing an exemplary embodiment of a mechanical stop.

FIG. 12 illustrates the adjustable sheath assembly 20 of the balloon catheter assembly 10, further comprising a mechanical stop. The mechanical stop may comprise an annulus 23 and a block 38. A sheath lumen may be defined as the opening between the outer surface of balloon 15 and the expanded portion 22a. In exemplary embodiments of the present invention, there may be no sheath lumen, as the sheath 22 substantially fits the curvature of the balloon 15. The annulus 23 may be located on the distal end of the expanded portion 22a. The annulus 23 may comprise an annual member located on the inner surface of the expanded portion 22a having a thickness such that it protrudes inwardly, thereby restricting the sheath lumen. The stop 38 may comprise a corresponding annual member 38 located on the outer diameter of the balloon 15, though any shape capable of frictionally engaging the annulus 23 is contemplated. The outer dimension of the stop 38 has an outer diameter larger that the lumen created by the annulus 23. In such an embodiment, the outer diameter of the corresponding stop 38 is configured such that it frictionally engages annulus 23, thereby preventing the balloon 15 from extending beyond the annulus 23.

Figure 13:
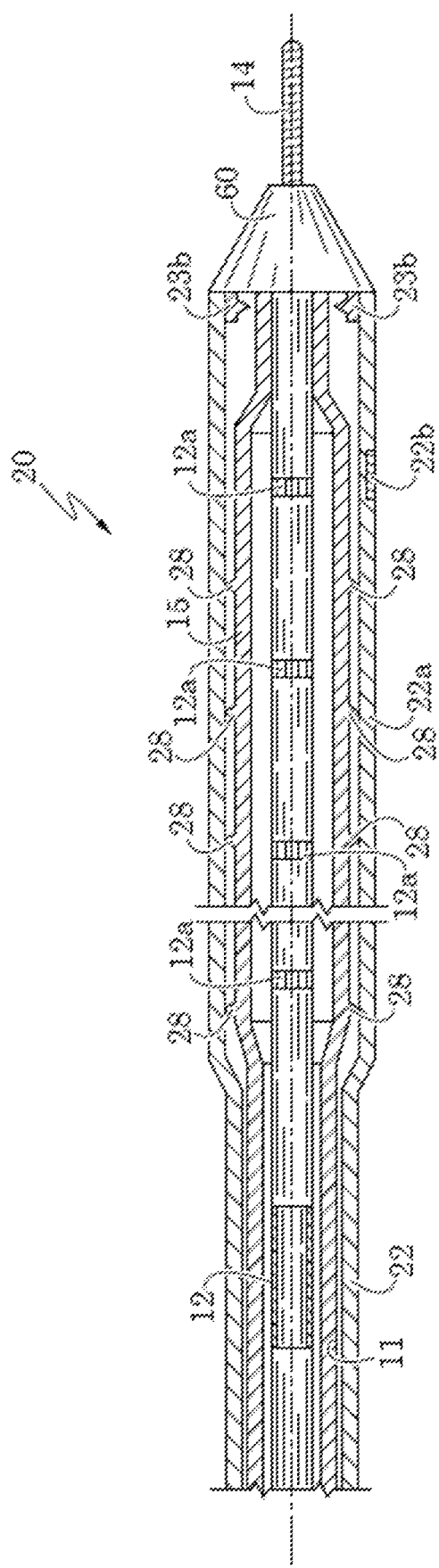
FIG. 13 is a sectional elevation view similar to FIG. 12 showing another exemplary embodiment of the mechanical stop.

FIG. 13 illustrates another exemplary embodiment of the present invention in which the assembly 10 further comprises one or more ridges 28 located on the outer surface of the balloon 15 that extend vertically therefrom. The mechanical stop may comprise an annular shaped pointed member 23b that it protrudes inwardly from the inner surface of the distal end of the expanded portion 22a, thereby restricting the sheath lumen, and the ridges 28. Further, the pointed shape of the pointed member 23b may be complementary to the shape of each of the ridges 28. As the balloon 15 is advanced relative to the sheath 22, the pointed member 23b may selectively secure the balloon 15 by frictionally engaging each of the ridges 28. In exemplary embodiments, the ridges 28 are formed as part of the balloon 15. Alternatively, the ridges 28 may be separately formed and attached to the outer diameter of balloon 15. Any number of ridges 28 is contemplated. Additionally, the ridges 28 may be equally spaced apart along balloon 15, though any spacing is contemplated. The series of ridges 28 may be comprised of a sufficiently rigid material such that each ridge 28 may not pass through the lumen created by the pointed member 23b without the user exerting a force on the assembly 10 such that the ridge 28 or the pointed member 23b may be sufficiently deformed to pass though the lumen created by pointed member 23b. This force may be exerted by the user directly on the outer member 11. Alternatively, this force may be exerted by the user on the outer member by use of the clamp 21.

Figure 14:
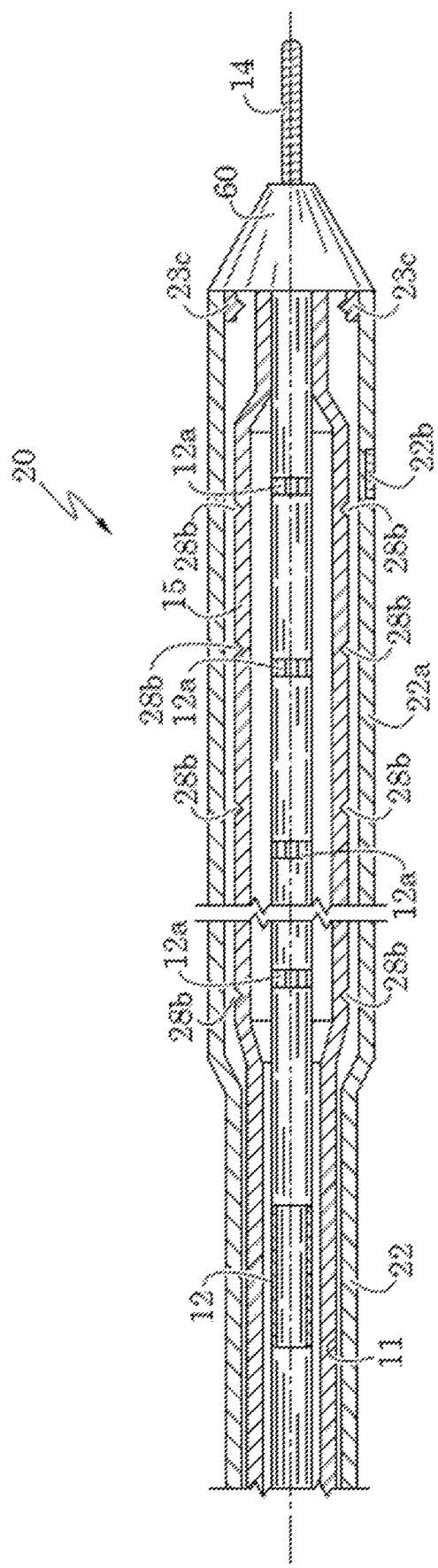
FIG. 14 is a sectional elevation view similar to FIG. 12 showing another exemplary embodiment of the mechanical stop.

FIG. 14 illustrates another exemplary embodiment wherein the balloon 15 comprises a series of valleys 28b located on the outer diameter of the balloon 15. The valleys 28b reduce the thickness of the balloon 15 such that outer diameter of the balloon 15 is reduced. Any number of valleys 28b is contemplated. Said valleys 28b may be equally spaced apart along the balloon 15, though any spacing is contemplated. A pointed member 23c may selectively secure movement of the balloon 15 relative to the sheath 22 by frictionally engaging each of the valleys 28b as they move through the lumen created by the pointed member 23c. The shape of the pointed member 23b may be formed complementary to the void created by each of the valleys 28b. The pointed member 23c may be comprised of a sufficiently flexible material such that each of the valleys 28b may not pass through the lumen created by the pointed member 23c until the user exerts force on the assembly such that the pointed member 23c or the balloon 15 is sufficiently deformed to permit each of the series of valleys 28b to pass through the lumen created by the pointed member 23c. This force may be exerted by the user directly on the outer member 11. Alternatively, this force may be exerted by the user on the outer member by use of the clamp 21.

Figure 15:
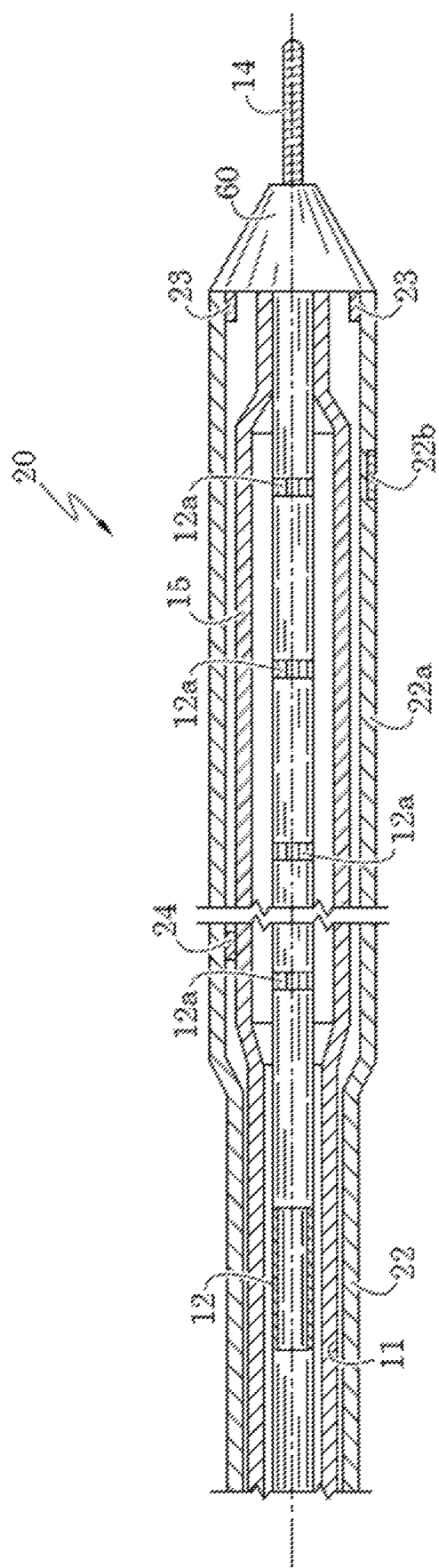
FIG. 15 is a sectional elevation view similar to FIG. 12 showing another exemplary embodiment of the mechanical stop.

FIG. 15 illustrates another exemplary embodiment of the present invention wherein the mechanical stop comprises a block 24, which may be attached to the balloon 15. The block 24 may be attached to the outer diameter of the balloon 15. The block 24 may be in the shape of a "T" such that the vertical section of the "T" extends vertically from the outer surface of balloon 15 and the horizontal portion of the "T" is curved and secured to the outer surface of the balloon 15, though any shape is contemplated. As the balloon 15 is extended from the expanded portion 22a, the block 24 frictionally engages the mechanical stop 23. In other exemplary embodiments of the present invention, the block of any shape may be used in place of the block 24.

Figure 16:
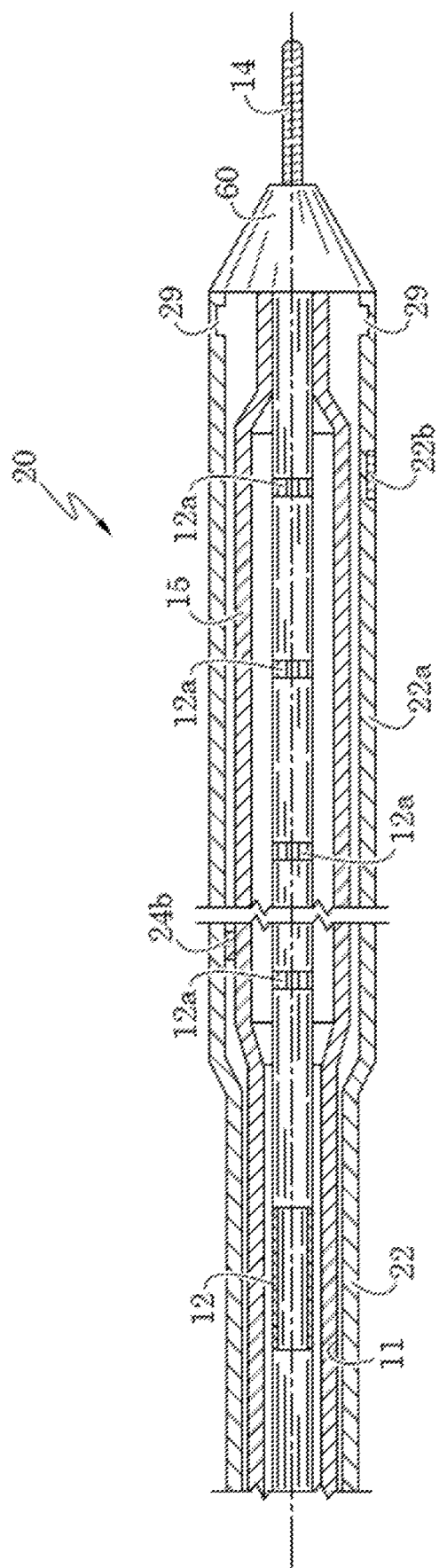
FIG. 16 is a sectional elevation view similar to FIG. 12 showing another exemplary embodiment of the mechanical stop.

FIG. 16 illustrates another exemplary embodiment of the mechanical stop comprising a circumferential slot 29 located on the inner surface of the expanded portion 22a. The slot 29 may be configured to accommodate and frictionally engage a collapsible block 24b such that as the balloon 15 is extended from the expanded portion 22a, the collapsible block 24b expands and enters the slot 29, thereby preventing the balloon 15 from further extending relative to the expanded portion 22a. In exemplary embodiments of the present invention, a collapsible orthotope, column, "T", or other shape collapsible device may be used. The collapsible block 24b, or the portion of the collapsible block 24b extending into the slot 29, may be spring loaded or otherwise biased into an expanded position.

Figure 17:
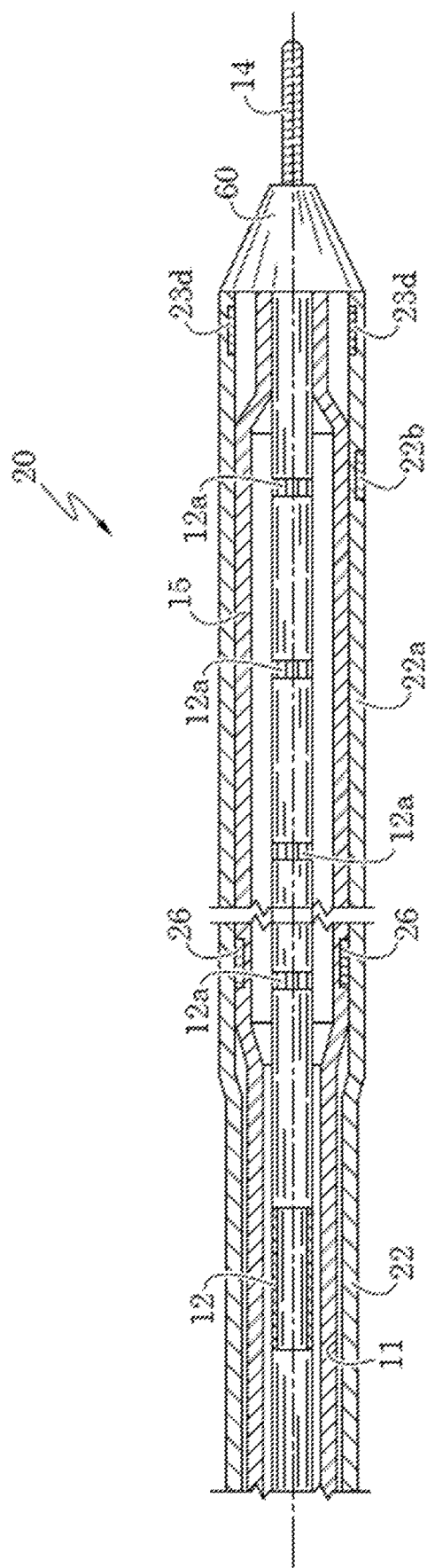
FIG. 17 is a sectional elevation view similar to FIG. 12 showing another exemplary embodiment of the mechanical stop.

FIG. 17 illustrates another exemplary embodiment in which the mechanical stop comprises a first and second portion 26 and 23d. The first and second portion 26 and 23d may be located on the outer surface of the balloon 15 and the inner surface of the sheath 22, respectively, and may comprise a surface or a coating with a relatively high coefficient of friction. The remainder of the balloon 15 and the sheath 22 may further comprise a surface or a coating with a relatively low coefficient of friction such as a polymer, silicone, any kind of lubricant, or the like. The first and second portions 26 and 23d may comprise a rubber, polymer, or the like. Further, the first and second portions 26 and 23d may be comprised of a surface, a coating, or a surface texture to increase the coefficient of friction such as bumps or the like. The first portion 26 may be located towards the proximal end of the balloon 15 relative to the clamp 21, though any location is contemplated. The second portion 23d may be located towards the distal end of the sheath 22 relative to the clamp 21, though any location is contemplated. The balloon 15 may extend relative to the sheath 22 until the first portion 26 encounters and frictionally engages the second portion 23d, thereby preventing the balloon 15 from traveling beyond.

Those having skills in the art will realize that these embodiments are merely exemplary and that any device may be utilized with the present invention to prevent a section of balloon 15 from extending from the sheath 22. As such, any shape or design of mechanical stop capable of preventing a portion of balloon 15 from escaping the sheath 22 is contemplated. Further, those skilled in the art will recognize that a combination of the aforementioned embodiments may be utilized.

FIG. 18 is an enlarged, side, sectional view of the adjustable sheath assembly 20 with the balloon 15 removed to better illustrate an exemplary balloon recapture element. The balloon recapture element may be a rounded or smoothed distal end 70 of the sheath 22. Additionally, or in the alternative, the balloon recapture element may be a tapered or angled distal end 70 of the sheath. The rounded, smoothed, tapered, or angled distal end 70 may provide less frictional resistance and reduce the potential for wear and/or tearing of the balloon 15 when the balloon is being placed back into the sheath 22 and/or the exposed length of the balloon 15 from the sheath 22 is being adjusted.

FIG. 19 illustrates another exemplary embodiment of the balloon recapture element. The balloon recapture element may comprise rifling 74 located on the inner surface of the sheath 22. In exemplary embodiments of the present invention, the rifling 74 is spiral shaped and extends along at least a portion of the sheath 22. However, there may be any number of rifles 74, along any length of the sheath 22. Further, the rifling 74 may be in any configuration, including but not limited to, any slope angled between 0 degrees and 90 degrees.

FIG. 19B and FIG. 19C illustrate an exemplary pleated balloon 15' for use with the rifling 74 of FIG. 19. In exemplary embodiments of the present invention, the rifling 74 may be configured to mate with a number of pleats 72 located on the outer surface of the balloon 15'. Any size, number, shape, or configuration of the pleats 72 is contemplated. The pleats 72 may be configured to fit into the rifling 74 such that the distance the balloon 15' protrudes from the sheath 22 may be incrementally and predictably increased or decreased by advancing or retracting the balloon 15' along the rifling 74 relative to the sheath 22. In other exemplary embodiments of the present invention, the rifling 74 may mate and interact with the ridges 28, blocks 24, collapsible blocks 24b, valleys 28b, stop 38, or other stop mechanism. Additionally, the rifling 74 may permit the balloon 15' to be neatly folded and repackaged upon retraction into the sheath 22. For example, without limitation, the rifling 74 may be patterned such that the balloon 15' is forced along a track that encourages or forces the balloon 15' to be folded in a desired manner for efficient packing. Such folding and packing may be further facilitated by preexisting creases in the balloon 15'. Regardless, the rifling 74 may reduce or prevent the potential for wear, tearing, or premature failure of the balloon 15', thus permitting the balloon 15' to be successively redeployed at the same or other treatment sites.

FIG. 20 and FIG. 20B illustrate another embodiment of the balloon recapture element where the sheath 22 may be formed with a funnel-shaped tip. The funnel-shaped tip may take the form of an enlarged section 76 whereby the diameter is increased over a length of the sheath 22 and then the diameter is held constant over a second length of the sheath 22. Alternatively, the funnel-shaped tip may take the form of a diametrically increasing length 78 of the sheath 22. In this way the balloon 15 may be gradually forced to reduce in size as it travels back into the sheath 22, resulting in a more easily recaptured balloon 15. This may reduce or prevent the potential for wear, tearing, or premature failure of the balloon 15, thus permitting the balloon 15 to be successively redeployed at the same or other treatment sites.

Figure 21:
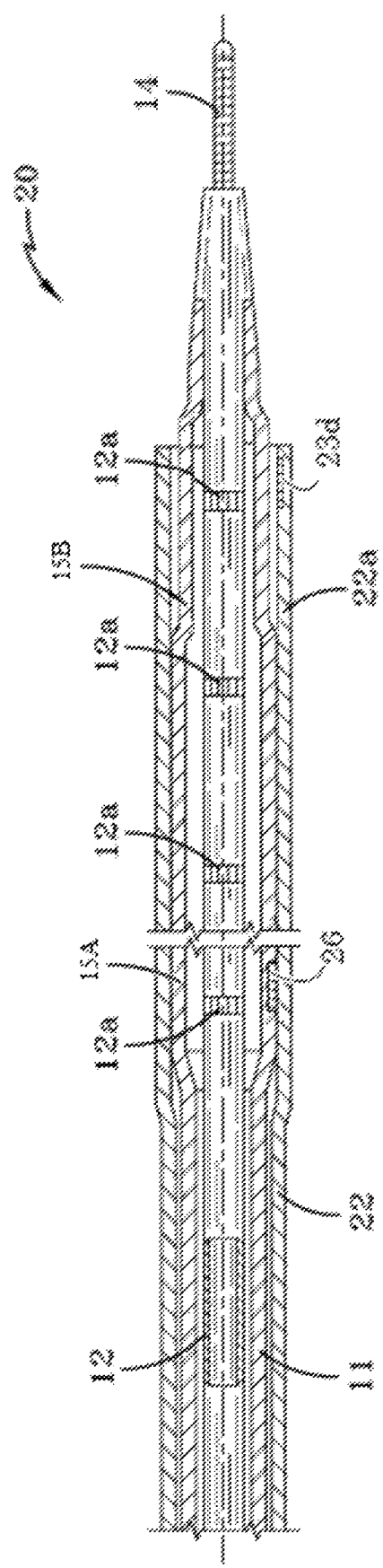
FIG. 21 is a sectional elevation view similar to FIG. 12 showing another exemplary embodiment of the balloon.

FIG. 21 is a sectional elevation view similar to FIG. 12 showing another exemplary embodiment of the balloon 15. In particular, the balloon 15 may comprise a proximal portion 15A and a distal portion 15B. While the proximal portion 15A is illustrated as having a larger outer diameter as compared to the distal portion 15B, it is contemplated that the proximal portion 15A and the distal portion 15B may have the same size outer diameter. It is further contemplated that the proximal portion 15A may have a smaller outer diameter as compared to the distal portion 15B.

The proximal portion 15A may be located proximal to the clamp 21 relative to the distal portion 15B. In exemplary embodiments, the proximal portion 15A may be relatively compliant compared to the distal portion 15B. This may permit the proximal portion 15A to expand against the inner surface of the sheath 22, such as the expanded portion 22a. This may prevent the proximal portion 15A of the balloon 15 from escaping the sheath 22. In other exemplary embodiments, the distal portion 15B may be relatively compliant compared to the proximal portion 15A. This may permit the distal portion 15B to expand to a larger size before the proximal portion 15A contacts the inner surface of the sheath 22. The proximal portion 15A may be comprised of a more compliant material than the distal portion 15B.

The proximal portion 15A may comprise the first portion 26 or a similar area having a relatively high coefficient of friction. Likewise, the expanded portion 22a of the sheath 22 may comprise the second portion 23d or similar area having a relatively high coefficient of friction. For example, without limitation, the first and second portions 26 and 23d may be comprised of a rubber, a material having a high degree of texture, or the like. In this way, when the proximal portion 15A is expanded, the first portion 26 is placed into contact with the second portion 23d. As the pressure of the balloon 15 increases, the normal forces between the first and second portions 26 and 23d may increase, thereby increasing the associated frictional forces. Any number of first and second portions 26 and 23d may be located on the balloon 15 at any location. It is further contemplated that the entire proximal portion 15A may be comprised of a material having a relatively high coefficient of friction.

Alternatively, or in addition, the proximal portion 15A and the distal portion 15B may have different size outer diameters. In one exemplary embodiment, the proximal portion 15A may be larger than the distal portion 15B such that the proximal portion 15A first comes into contact with the inner surface of the sheath 22. In another exemplary embodiment, the distal portion 15B is larger than the proximal portion 15A. In this way, the balloon 15 may be permitted to expand into a larger size before the proximal portion 15A contacts the inner surface of the sheath 22. These are merely examples and are not intended to be limiting. It is contemplated that the balloon 15 may be any size or shape and comprise any number of characteristic (compliance, strength, pressure rating, etc.) and may contain any number of portions having different sizes and shapes and comprise any number of characteristics. It is specifically contemplated that the proximal portion 15A and the distal portion 15B may have the same size outer diameter.

Figure 22:
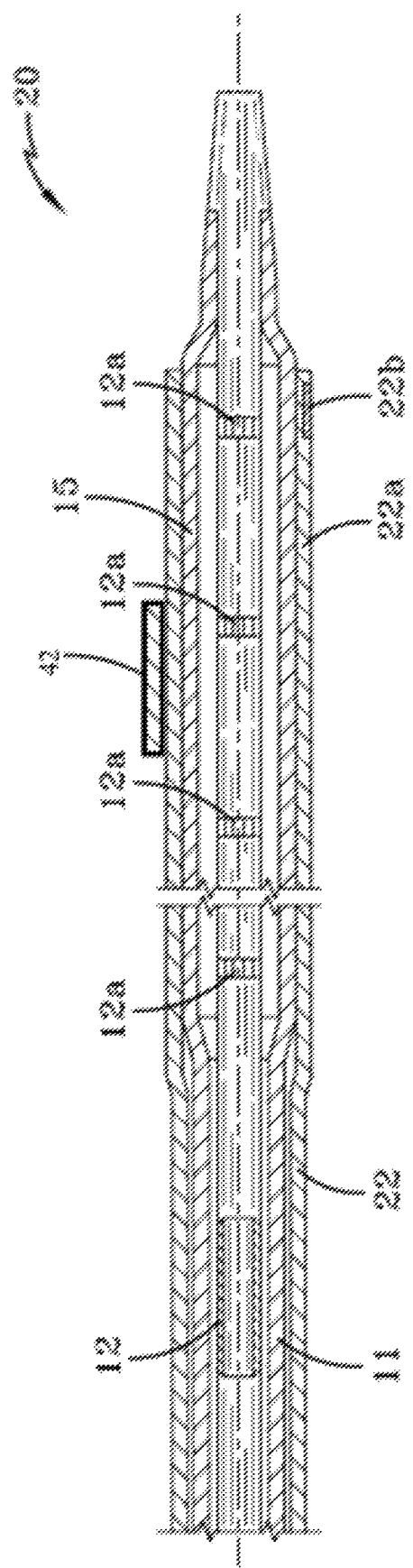
FIG. 22 is a sectional elevation view similar to FIG. 12 showing another exemplary embodiment of the balloon.

FIG. 22 illustrates another exemplary embodiment of the sheath assembly 20. The sheath assembly may comprise an attachment device 42. The attachment device 42 may be located on the outer surface of the sheath 22. In exemplary embodiments, the attachment device 42 may extend along the outer surface of the expanded portion 22a. The attachment device 42 may be configured to accommodate the guide wire 14. In particular, the attachment device 42 forms a tube, slit, or channel configured to accommodate the guide wire 14. The tube, slit, or channel, for example without limitation, may be tubular in shape, U-shaped, V-shaped, or the like. The attachment device 42 may facilitate the use of a guide wire 14 to position the balloon catheter assembly 10. The attachment device 42 may further facilitate the exchange of the balloon catheter assembly 10 with other medical devices.

Figure 23:
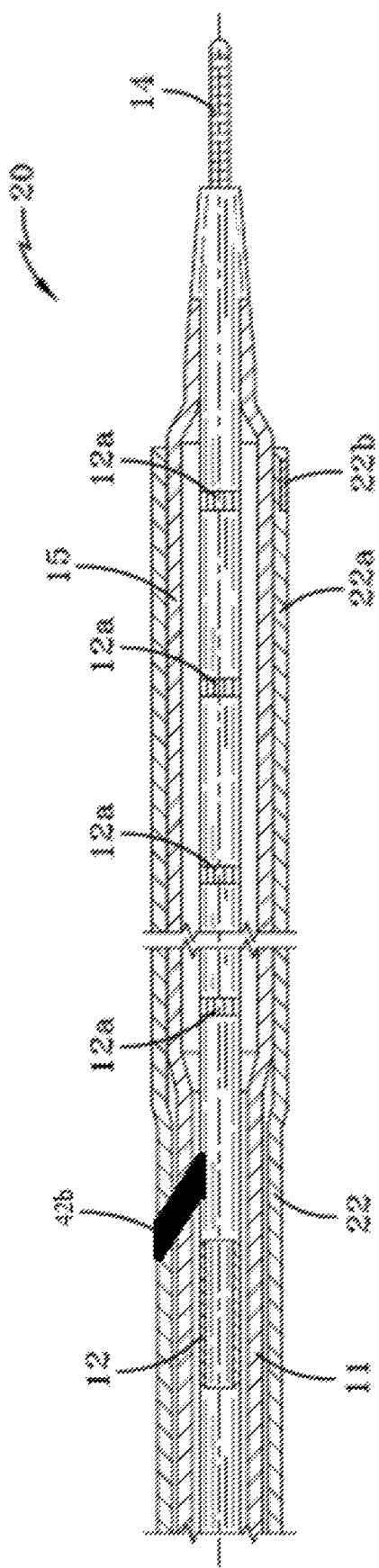
FIG. 23 is a sectional elevation view similar to FIG. 12 showing another exemplary embodiment of the balloon.

FIG. 23 illustrates another exemplary embodiment of an attachment device 42b. In exemplary embodiments, the attachment device 42b may be a pass-through device. The attachment device 42b may be a tube, slit, or channel that permits the guide wire 14 to exit through the sheath 22, the balloon 15, and into the inner member 12 closer to the distal end of the adjustable sheath assembly 20. Advantageously, this approach requires a shorter guide wire 14. This stands in contrast to the over-the-wire approach (also contemplated), where the guide wire 14 exits near the clamp 21. It is contemplated that the attachment device 42b may be located anywhere along the catheter assembly 10. For example, without limitation, the attachment device 42b may be located proximal to the balloon 15 such that the attachment device 42b permits the guide wire 14 to pass through the sheath 22 and into the inner member 12. In exemplary embodiments, the guide wire 14 may enter through the attachment device 42b, pass through the inner member 12, and exit the distal end of the catheter assembly 10. In still other exemplary embodiments, the attachment device 42b may be configured to permit the guide wire 14 to extend through the sheath but not into the inner member 12.

Figure 24:
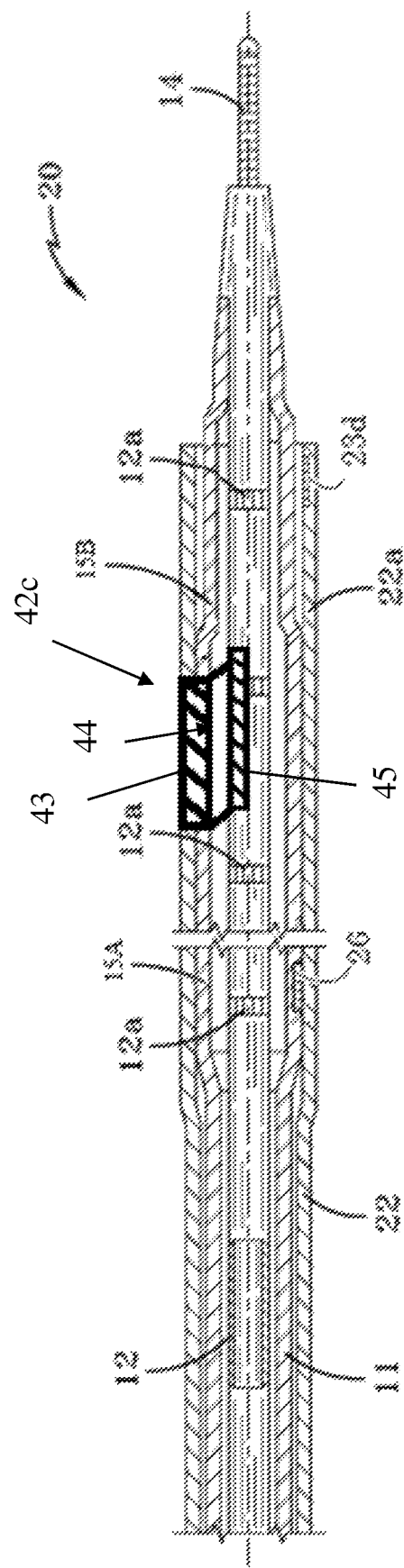
FIG. 24 is a sectional elevation view similar to FIG. 12 showing another exemplary embodiment of the balloon.
Figure 25:
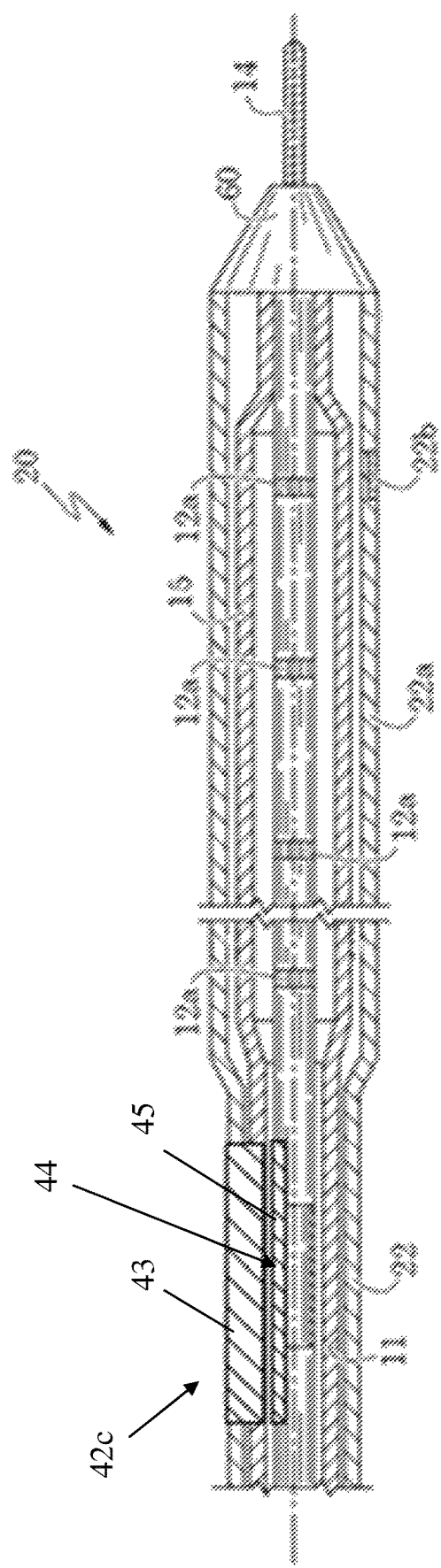
FIG. 25 is a sectional elevation view similar to FIG. 12 showing another exemplary embodiment of the balloon.

FIG. 24 and FIG. 25 illustrate other exemplary embodiments of an attachment device 42c. In exemplary embodiments, the attachment device 42c may comprise a first slit 43 located along the sheath 22. The first slit 43 may be located along the expanded portion 22a, however any location is contemplated. In other exemplary embodiments, the first slit 43 may be located along the portion of the sheath 22 between the expanded portion 22a and the clamp 21. Stated another way, the first slit 43 may be located on the portion of the sheath 22 not housing the balloon 15.

The first slit 43 may be any size or shape. In exemplary embodiments, the first slit 43 is sized to substantially match the length of the balloon 15. In this way, the guide wire 14 will not get trapped or kinked when the balloon 15 is moved relative to the sheath 22. In other exemplary embodiments, the first slit 43 is sized to accommodate the guide wire 14. In such embodiments, additional guide wire 14 may be fed into or out of the attachment device 42c to accommodate movement of the balloon 15 relative to the sheath 22. In such embodiments, the first slit 43 may be shaped as a circle, though any shape is contemplated.

The first slit 43 may also extend into the balloon 15, however such is not required. A second slit 45 may be located in the inner member 12, though such is not required. The second slit 45 may also be sized to substantially match the length of the balloon 15. In exemplary embodiments, the first slit 43 is sized to substantially match the length of the balloon 15. In this way, the guide wire 14 will not get trapped or kinked when the balloon 15 is moved relative to the sheath 22. In other exemplary embodiments, the second slit 45 may be sized to accommodate the guide wire 14. In such embodiments, additional guide wire 14 may be fed into or out of the attachment device 42c to accommodate movement of the balloon 15 relative to the sheath 22. In such embodiments, the first slit 43 may be shaped as a circle, though any shape is contemplated. The second slit 45 may be the same or a different size and shape than the first slit 43.

A channel 44 may extend between the first slit 43 and the second slit 45, however such is not required. The channel 44 may be configured to accommodate the guide wire 14. The channel 44 may also be sized to substantially match the length of the balloon 15. In other exemplary embodiments, the channel 44 may be sized to accommodate the guide wire 14. The channel 44 may be the same or a different size than the first slit 43 and/or the second slit 45. The channel 44 may be formed by side walls extending between the first slit 45 and the second slit 45. However, in other exemplary embodiments, the channel 44 is defined by the space between the first slit 45 and the second slit 45.

The guide wire 14 may enter the adjustable sheath assembly 20 through the distal end thereof and may exit the adjustable sheath assembly 20 through one or more of the: first slit 43, the channel 44, and the second slit 45.

The attachment device 42, 42b, or 42c may permit a shorter guide wire 14 to be used. Normally, the guide wire 14 must extend from the treatment site all the way back to the clamp 21 or the entrance/exit point into the persons' vascular system. Particularly in below the knee applications, which are contemplated, this may require a long guide wire 14. Such guide wires 14 may not be commercially available or may be expensive. Additionally, such guide wires may be cumbersome to use and difficult to control. The use of the attachment device 42, 42b, or 42c may provide an exit point for the guide wire 14 closer to the distal end of the adjustable sheath assembly 20 such that a shorter guide wire 14 may be used. This may permit use with shorter guide wires 14 which may be cheaper, more readily available, and easier to control.

It is notable that any of the aforementioned balloon recapture elements illustrated and described with respect to FIGS. 18-23 may be used in combination with one another and in combination with any or all of the embodiments described herein.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. An intravascular balloon catheter device comprising:
an inner member;
an outer member disposed about the inner member;
a balloon having a proximal portion connected to the outer member and a distal portion connected to the inner member;
a sheath adapted for movement relative to the balloon so as to selectively expose the distal portion of the balloon for inflation;
a first area located on an inner surface of the sheath; and
a second area located on the outer surface of the proximal portion;
wherein the first and second areas are comprised of a material having a relatively high coefficient of friction as compared to a remainder of the balloon and sheath;
wherein the sheath is configured to prevent the proximal portion of the balloon from inflating to a diameter larger than the sheath;
wherein the proximal portion of the balloon is configured to contact an inner surface of the sheath upon inflation.

2. The device of claim 1 further comprising:
a clamp configured to selectively secure the sheath at a desired position relative to the balloon such that the distal portion of the balloon is exposed for inflation and the proximal portion of the balloon remains located within the sheath.

3. The device of claim 2 further comprising:
an adapter located adjacent to the clamp and configured to facilitate access to both the outer member and the inner member.

4. The device of claim 3 wherein:
the adapter comprises a luer lock.

5. The device of claim 4 wherein:
the luer lock is configured to receive a cartridge comprising pressurized carbon dioxide.

6. The device of claim 4 wherein:
the luer lock is configured to receive a syringe comprising a biocompatible fluid.

7. The device of claim 1 wherein:
the proximal portion of the balloon is configured to inflate to a first maximum diameter;
the distal portion of the balloon is configured to inflate to a second maximum diameter; and
the first maximum diameter is smaller than the second maximum diameter.

8. The device of claim 1 wherein:
the proximal portion of the balloon has a first outer diameter;
the distal portion of the balloon has a second outer diameter; and
the first outer diameter is smaller than the second outer diameter.

9. The device of claim 1 further comprising:
an attachment device configured to permit a guide wire to pass through the sheath and into the inner member.

10. The device of claim 1 further comprising:
a coating comprising a therapeutic agent located on the outer surface of at least the distal portion of the balloon, wherein at least the distal portion of the balloon fits snugly into the sheath so as to provide a substantially watertight engagement between at least the distal portion of the balloon and the sheath when the distal portion of the balloon is located within the sheath.

11. An intravascular balloon catheter device comprising:
an outer member;
a balloon affixed to a distal end of the outer member and configured to be selectively inflated to a first diameter and selectively deflated to a second diameter, wherein the first diameter is larger than the second diameter;
an inner member disposed within the outer member;
a sheath disposed about the outer member and configured for movement relative to the balloon so as to selectively expose a distal portion of the balloon for inflation while a proximal portion of the balloon remains in the sheath;
a clamp comprising a first and second actuator arm that are supported within a housing; and a plurality of spaced indications located on the outer member, wherein the first and second actuator arms are configured to selectively engage the plurality of spaced indentations.

12. The device of claim 11 wherein:

the proximal portion of the balloon is comprised of a material having a relatively high coefficient of friction as compared to the distal portion of the balloon.

13. The device of claim 11 further comprising:

a coating comprising a therapeutic agent located on the outer surface of at least the distal portion of the balloon, wherein at least the distal portion of the balloon fits snugly into the sheath so as to provide a substantially watertight engagement between at least the distal portion of the balloon and the sheath when the distal portion of the balloon is located within the sheath.

14. The device of claim 11 wherein:

the proximal portion of the balloon is more compliant than the distal portion of the balloon.

15. An intravascular balloon catheter device comprising:

an inner member;

an outer member disposed about the inner member;

a balloon having a proximal portion connected to the outer member and a distal portion connected to the inner member;

a sheath adapted for movement relative to the balloon so as to selectively expose the distal portion of the balloon for inflation; and an attachment device located on the outer surface of the sheath and configured to receive a guide wire, wherein the attachment device comprises a slit located along the sheath to provide an exit point for the guide wire and sized to match the length of the balloon;

wherein the sheath is configured to prevent the proximal portion of the balloon from inflating to a diameter larger than the sheath.

16. The intravascular balloon catheter device of claim 15 wherein:

at least the distal portion of the balloon fits snugly into the sheath so as to provide a substantially watertight engagement between at least the distal portion of the balloon and the sheath when the distal portion of the balloon is located within the sheath.

* * * * *